US010221435B2

(12) United States Patent
Araki et al.

(10) Patent No.: US 10,221,435 B2
(45) **Date of Patent: *Mar. 5, 2019**

(54) DNA ENCODING NOVEL ENZYME HAVING D-SERINE SYNTHASE ACTIVITY, METHOD OF PRODUCING THE ENZYME AND METHOD OF PRODUCING D-SERINE BY USING THE SAME

(71) Applicant: Mitsui Chemicals, Inc., Minato-ku, Tokyo (JP)

(72) Inventors: Tadashi Araki, Chiba (JP); Tomonori Hidesaki, Funabashi (JP); Seiichi Watanabe, Mobara (JP); Keita Nishida, Gunma (JP); Kiyoteru Nagahara, Omuta (JP); Mitsuo Koito, Omuta (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/615,336

(22) Filed: Jun. 6, 2017

(65) Prior Publication Data

US 2017/0327853 A1 Nov. 16, 2017

Related U.S. Application Data

(60) Continuation of application No. 14/928,428, filed on Oct. 30, 2015, now Pat. No. 9,695,452, which is a continuation of application No. 13/034,098, filed on Feb. 24, 2011, now Pat. No. 9,212,376, which is a division of application No. 11/665,194, filed as application No. PCT/JP2005/018906 on Oct. 7, 2005, now Pat. No. 7,919,285.

(30) Foreign Application Priority Data

Oct. 13, 2004 (JP) ................................ 2004-298344

(51) Int. Cl.
*C12P 13/06* (2006.01)
*C12N 9/10* (2006.01)

(52) U.S. Cl.
CPC ............ *C12P 13/06* (2013.01); *C12N 9/1014* (2013.01)

(58) Field of Classification Search
CPC ............................... C12P 13/06; C12N 9/1014
See application file for complete search history.

(56) References Cited

U.S. PATENT DOCUMENTS

| | | | | |
|---|---|---|---|---|
| 7,186,532 | B2 | 3/2007 | Ikeda et al. | |
| 7,919,285 | B2 | 4/2011 | Araki | |
| 9,212,376 | B2 * | 12/2015 | Araki ..................... | C12P 13/06 |

FOREIGN PATENT DOCUMENTS

| | | | |
|---|---|---|---|
| EP | 1 331 274 | A1 | 7/2003 |
| JP | 58-116690 | A | 7/1983 |
| JP | 05-168484 | A | 7/1993 |

OTHER PUBLICATIONS

Broun et al. "Catalytic plasticity of fatty acid modification enzymes underlying chemcial diversity of plant lipids," Science 1998 vol. 282, 1315-1317.

Chica et al, "Semi-rational approaches to engineering enzyme activity: combining the benefits of directed evolution and rational design," Curr. Opi, Biotechnol. 2005, vol. 16: 378,384.

Database EMBL, "Achromobacter xylosoxidans, D-threonine aldolase", Aug. 6, 2000, XP002451106, retrieved from EBI, Database Accession No. AB026892.

Database EMBL, "D-threonine aldolase", Jan. 21, 1994, XP002451107, retrieved from EBI, Database Accession No. AAQ46816.

Devos et al. "Proctial limits of function prediction," Proteins: Structure, Function, and Genetics, 2000, vol. 41: 98-107.

Ji-Quan Liu et al., "Diversity of microbial threonine aldolases and their application", Journal of Molecular Catalysis β Enzymatic, Sep. 4, 2000, pp. 107-115, vol. 10, No. 1-3, XP009089566, ISSN: 1381-1177.

Ji-Quan Liu et al.; "A Novel Metal-activated Pyridoxal Enzyme with a Unique Primary Structure, Low Specificity D-Threonine Aldolase from *Arthrobacter* sp. Strain DK-38"; The Journal of Biological Chemistry; 1998; pp. 16678-16685; vol. 273, No. 27.

Michihiko Kataoka et al., "Isolation and characterization of D-threonine aldolase, a pyridoxal-5'-phosphate-dependent enzyme from Arthrobactersp. DK-38", European Journal of Biochemistry, 1997, pp. 385-393, vol. 248, No. 2, XP001536684, ISSN: 0014-2956.

Seffernick et al. "Melamine deaminase and Atrazine chlorohydrolase: 98 percent identical but functionally different," J. Bacteriol. 2001, vol. 183(8): 2405-2410.

Sen et al. "Developments in directed evolution for improving enzyme functions." Appl. Biochem. Biotechnol. 2007, vol. 143: 212-223.

Whisstock et al. "Prediction of protein function from protein sequence," Q. Rev. Biophysics, 2003, vol. 36(3): 307-340.

Witkowski et al. "Conversion of b-ketoacyl synthase to a malonyl decarboxylase by replacement of the active-site cysteine with glutamine," Biochemistry, 1999, vol. 38, 11643-11650.

* cited by examiner

*Primary Examiner* — Ganapathirama Raghu
(74) *Attorney, Agent, or Firm* — Buchanan, Ingersoll & Rooney PC

(57) ABSTRACT

This invention relates to DNA encoding a novel enzyme having activity of synthesizing D-serine from formaldehyde and glycine, recombinant DNA constructed by integrating such DNA into a vector, a transformant transformed with the recombinant DNA, and a method for producing D-serine from formaldehyde and glycine with the use of the enzyme.

6 Claims, 2 Drawing Sheets

Specification includes a Sequence Listing.

M: Marker
1: MT-11015 Cell disruption solution
2: MT-11015 Cell disruption residue
3: MT-11016 Cell disruption solution
4: MT-11016 Cell disruption residue
5: MT-11017 Cell disruption solution
6: MT-11017 Cell disruption residue M: Molecular weight marker
1: Solution subjected to ultrasonic disruption
2: Ion exchange purification (Q XL)
3: Hydrophobic chromatography purification (Phenyl FF)

DNA ENCODING NOVEL ENZYME HAVING D-SERINE SYNTHASE ACTIVITY, METHOD OF PRODUCING THE ENZYME AND METHOD OF PRODUCING D-SERINE BY USING THE SAME

TECHNICAL FIELD

The present invention relates to DNA encoding a novel enzyme having activity of synthesizing D-serine from formaldehyde and glycine, recombinant DNA constructed by integrating such DNA into a vector, a transformant transformed with the recombinant DNA, a novel enzyme having activity of synthesizing D-serine from formaldehyde and glycine, and a method for producing D-serine from formaldehyde and glycine with the use of the enzyme.

BACKGROUND ART

D-serine has been known as a compound that is useful as a synthesis intermediate for medicaments such as D-cycloserine.

Hitherto, as an enzyme having activity of synthesizing D-serine from formaldehyde and glycine, only D-threonine aldolase (hereafter to be abbreviated as "DTA"), which is derived from *Arthrobacter* sp. DK-19, has been known (JP Patent Publication (Kokai) No. 58-116690 A (1983)).

With the use of such DTA, it has been reported that the amount of D-serine produced was 2.5 mmol when 50 mmol each of formaldehyde and glycine were subjected to reaction at 30° C. for 40 hours. (The yield relative to formaldehyde was merely 5%.)

Meanwhile, it has been reported that DTA derived from *Arthrobacter* sp. DK-38, which is a microorganism of the same genus *Arthrobacter*, has a broad substrate specificity that responds to D-threonine, D-β-hydroxyphenylserine, D-β-hydroxy-α-aminovaleric acid, and the like; however, it does not react with D-serine (see Eur. J. Biochem., 1997, 248, pp. 385-393).

In addition, it has been reported that D-β-hydroxyamino acids can be produced from glycine and an aldehyde compound with the use of DTA derived from the genus *Xanthomonas* (JP Patent Publication (Kokai) No. 5-168484 A (1993)). However, it has not been reported that D-serine can be synthesized from formaldehyde and glycine with the use of DTA derived from the genus *Xanthomonas*.

DISCLOSURE OF THE INVENTION

In view of the aforementioned background art, it is an objective of the present invention to provide DNA encoding a novel enzyme having activity of synthesizing D-serine from formaldehyde and glycine, a recombinant DNA constructed by integrating such DNA into a vector, a transformant transformed with the recombinant DNA, a novel enzyme having an activity of synthesizing D-serine from formaldehyde and glycine, and a method for producing D-serine from formaldehyde and glycine with the use of the enzyme.

The present inventors thought that some unknown enzymes that have structures similar to those of known DTAs could be capable of synthesizing D-serine from formaldehyde and glycine. Thus, they examined information regarding the amino acid sequences of known DTAs. Accordingly, they have found information regarding the amino acid sequences of DTAs derived from the genera *Xanthomonas* (GenBank accession No. E05055), *Achromobacter* (GenBank accession No. AB026892), and *Arthrobacter* (GenBank accession No. AB010956). As a result of comparison and examination of these amino acid sequences, they have found that amino acid sequences corresponding to the N-terminal region and the C-terminal region of DTA are highly homologous to each other.

The present inventors designed primers based on these amino acid sequences of the N-terminal region and the C-terminal region. They then tried to amplify chromosome DNAs of a variety of microorganisms by PCR using the primers. Accordingly, they have succeeded in amplifying DNA encoding an enzyme having activity of synthesizing D-serine from formaldehyde and glycine with the use of a microorganism of the genus *Achromobacter.*

The amino acid sequence corresponding to the DNA is approximately 50% homologous to the amino acid sequence of known DTA derived from the genus *Achromobacter*, such that it significantly differs from the amino acid sequence of known DTA derived from the genus *Achromobacter*. Meanwhile, it is approximately 90% homologous to the amino acid sequence of known DTA derived from the genus *Xanthomonas*.

Next, the present inventors tried to synthesize D-serine by allowing formaldehyde to react with glycine using recombinant *Escherichia coli* that had been transformed with a recombinant DNA constructed by integrating the above novel DNA into a vector. Surprisingly, unlike the case of conventionally known DTA, they have found that D-serine can be synthesized with a reaction yield of as high as 70% or more from 100 mM glycine and 100 mM formaldehyde.

Further, when a D-serine accumulation reaction was carried out using the recombinant *Escherichia coli*, a small amount of L-serine was found to be produced.

When D-serine is used in a field in which it is necessary for medicine intermediates or the like to have high purity, it is not preferable that L-serine be mixed in D-serine. Formation of L-serine as a byproduct upon production of D-serine causes a significantly lowered purification yield of D-serine, since the solubility of DL-serine is lower than that of D-serine.

As a result of further examination to solve the above problems, the present inventors have found that formation of L-serine as a byproduct can be restrained by carrying out organic solvent treatment and/or heat treatment in the presence of divalent metal ions. In addition, they have found that, even without carrying out such treatment, formation of L-serine as a byproduct can be restrained by maintaining formaldehyde concentration at 150 mM or more during reaction. Furthermore, they have found that formation of L-serine as a byproduct can be restrained by using a microorganism lacking an L-serine synthase gene as a host producing DSA that is used for D-serine synthesis.

Based on the above findings, the present invention has been completed. Specifically, the present invention is as follows.

(1) DNA encoding a protein described in the following (a) or (b):

(a) a protein comprising an amino acid sequence set forth in SEQ ID NO: 4, 6, or 8; or (b) a protein comprising an amino acid sequence derived from the amino acid sequence of (a) by deletion, substitution, insertion, or addition of one to several amino acid residues and having enzyme activity of synthesizing D-serine from glycine and formaldehyde.

(2) DNA described in the following (a) or (b):

(a) DNA comprising a nucleotide sequence set forth in SEQ ID NO: 3, 5, or 7 in the Sequence Listing or a sequence complementary to the nucleotide sequence; or (b) DNA hybridizing under stringent conditions with a DNA fragment comprising a DNA sequence comprising at least 20 consecutive bases of the nucleotide sequence set forth in SEQ ID NO: 3, 5, or 7 in the Sequence Listing or of a sequence complementary to the nucleotide sequence and encoding an enzyme having an activity of synthesizing D-serine from glycine and formaldehyde.

(3) A recombinant DNA constructed by integrating the DNA described in (1) or (2) above into a vector.

(4) A transformant obtained by transforming a host cell using the recombinant DNA described in (3) above.

(5) The transformant described in (4) above, wherein the host cell to be transformed is a microorganism.

(6) The transformant described in (5) above, wherein the microorganism to be transformed is a D-serine-deaminase-deficient microorganism.

(7) A protein described in the following (a) or (b):

(a) a protein comprising an amino acid sequence set forth in SEQ ID NO: 4, 6, or 8; or (b) a protein comprising an amino acid sequence derived from the amino acid sequence of (a) by deletion, substitution, insertion, or addition of one to several amino acid residues and having an enzyme activity of synthesizing D-serine from glycine and formaldehyde.

(8) A method for producing an enzyme having activity of synthesizing D-serine from glycine and formaldehyde, wherein the transformant described in any one of (4) to (6) above is cultured such that a protein having enzyme activity of synthesizing D-serine from glycine and formaldehyde is collected from the obtained culture product.

(9) A method for producing D-serine, comprising allowing glycine to react with formaldehyde in the presence of the transformant described in any one of (4) to (6) above or a treated product thereof.

(10) A method for producing D-serine, comprising allowing glycine to react with formaldehyde in the presence of the protein described in (7) above.

(11) A method for producing D-serine, wherein D-serine is synthesized by allowing glycine to react with formaldehyde in the presence of a microorganism having activity of synthesizing D-serine from glycine and formaldehyde or a treated product thereof, comprising one or more means described in the following (i) to (iv) whereby formation of L-serine as a byproduct in a reaction solution is restrained in a manner such that L-serine accounts for 1.5 mol % or less relative to D-serine during the reaction:

(i) a method for allowing a microorganism having activity of synthesizing D-serine from glycine and formaldehyde to be subjected to an organic solvent treatment and/or heat treatment;

(ii) a method for controlling formaldehyde concentration in a reaction solution a) to 2M or less in a case in which an organic solvent treatment and/or heat treatment are/is carried out by the method (i) above and b) to from 150 mM to 2M inclusive in a case in which an organic solvent treatment and/or heat treatment are/is not carried out;

(iii) a method for using, as a catalyst, a microorganism comprising an enzyme having activity of synthesizing D-serine from glycine and formaldehyde and lacking a L-serine synthase gene; and (iv) a method for adding a microorganism comprising an enzyme having an L-serine deaminase activity to a reaction solution.

(12) The production method described in (11) above, wherein the organic solvent is at least one selected from the group consisting of formaldehyde, benzaldehyde, dichloroethane, and isopropyl alcohol.

(13) The production method described in (11) or (12) above, wherein the organic solvent treatment and/or heat treatment are/is carried out in the presence of divalent metal ions.

(14) The production method described in (13) above, wherein the divalent metals are one or more types of metals selected from the group consisting of magnesium, manganese, zinc, nickel, cobalt, and iron.

(15) The production method described in (11) above, wherein the microorganism having activity of synthesizing D-serine from glycine and formaldehyde is the transformant described in (5) or (6) above.

1. Obtaining a Gene of DNA Encoding a Novel Enzyme Having Activity of Synthesizing D-Serine from Formaldehyde and Glycine DNA comprising the amino acid sequence set forth in SEQ ID NO: 4, 6, or 8 in the Sequence Listing and encoding an enzyme having activity of synthesizing D-serine from glycine and formaldehyde (hereafter to be abbreviated as "DSA") can be obtained by extracting chromosomal DNA from, for example, *Achromobacter xylosoxidans* (ATCC9220), which is available from the American Type Culture Collection (12301 Parklawn Drive, Rockville, Md. 20852, U.S.A.), and *Achromobacter xylosoxidans* (NBRC13495) and *Achromobacter denitrificans* (Synonym: *Achromobacter xylosoxidans* subsp. *denitrificans*) (NBRC15125), which are available from the NITE Biological Resource Center of the National Institute of Technology and Evaluation (2-5-8 Kazusakamatari, Kisarazu-shi, Chiba, Japan) and carrying out PCR with the use of primers comprising the nucleotide sequences set forth in SEQ ID NOS: 1 and 2 in the Sequence Listing, respectively.

It is effective to improve amplification conditions in a manner such that a gene having a few mismatched bases can be amplified when carrying out PCR. For instance, a gene that is amplified with difficulty can be occasionally amplified by a method wherein the annealing temperature is controlled at a low temperature, by a method involving the addition of dimethyl sulfoxide (approximately 5%) to a PCR reaction solution, by a method using a PCR kit (e.g., GC-RICH PCR System produced by Roche) that is designed to readily amplify a GC-rich gene, or by a combination of the above methods or the like.

Specific examples of DNA encoding DSA include the DNA nucleotide sequence of a DTA gene derived from *Achromobacter xylosoxidans* (ATCC9220) set forth in SEQ ID NO: 3, the amino acid sequence (translated by such nucleotide sequence) set forth in SEQ ID NO: 4, the DNA nucleotide sequence of a DTA gene derived from *Achromobacter xylosoxidans* (NBRC13495) set forth in SEQ ID NO: 5, the amino acid sequence (translated by such nucleotide sequence) set forth in SEQ ID NO: 6, the DNA nucleotide sequence of a DTA gene derived from *Achromobacter denitrificans* (NBRC15125) set forth in SEQ ID NO: 7, and the amino acid sequence (translated by such nucleotide sequence) set forth in SEQ ID NO: 8.

In addition to the aforementioned DNAs encoding DSA, DNA encoding DSA may be derived from any types of organisms, as long as it hybridizes with a DNA fragment comprising a DNA sequence of at least 20 consecutive bases of the nucleotide sequence set forth in SEQ ID NO: 3, 5, or 7 in the Sequence Listing or of a sequence complementary to such nucleotide sequence under stringent conditions and it encodes a protein having DSA activity. For instance, even a silent DNA that does not function in an organism may be used as long as it can produce DSA by ligating such DNA that has been isolated to an adequate expression vector.

Further, even if no organism is specified, DNA encoding DSA can be obtained by allowing soil or the like that is used for template DNA to be directly subjected to PCR using the primers having the nucleotide sequences set forth in SEQ ID NOS: 1 and 2 in the Sequence Listing.

A specific example of DNA encoding DSA is obtained by a method wherein PCR is carried out using, for example, chromosome DNA of a microorganism that grows in a medium containing D-serine as a template and primers having the nucleotide sequences set forth in SEQ ID NOS: 1 and 2 in the Sequence Listing, such that DNA is amplified.

In addition, it is also possible to obtain DNA encoding a protein having DSA activity and comprising an amino acid sequence derived from the amino acid sequence set forth in SEQ ID NO: 4, 6, or 8 by deletion, substitution, insertion, or addition of one to several amino acid residues via introduction of adequate mutation such as deletion, substitution, insertion, and/or addition with the use of site-specific mutagenesis methods (Nucleic Acid Res., 10, p. 6487 (1982); Nucleic Acid Res., 13, p. 4431 (1985); Methods in Enzymol., 100, p. 448 (1983); Molecular Cloning $2^{nd}$ Ed., Cold Spring Harbor Laboratory Press (1989); PCR A Practical Approach IRL Press p. 200 (1991); Current Protocols in Molecular Biology, John Wiley & Sons (1987-1997); Proc. Natl. Acad. Sci., USA, 79, p. 6409 (1982); Gene, 34, 315 (1985); and Proc. Natl. Acad. Sci., USA, 82, p. 488 (1985)) or the like, as long as the nucleotide sequence set forth in SEQ ID NO: 3, 5, or 7 in the Sequence Listing or a sequence complementary thereto can hybridize under stringent conditions and such mutation does not influence the activity of the enzyme to be encoded.

Deletion, substitution, insertion, or addition of amino acid residues described herein can be carried out by the aforementioned site-specific mutagenesis methods that were known techniques prior to the filing of the present application. In addition, the term "one to several amino acid residues" indicates a number of amino acids that allows deletion, substitution, insertion, or addition of amino acid residues (for example, 1 to 5 amino acid residues and preferably 1 to 3 amino acid residues) to be carried out by site-specific mutagenesis methods.

Examples of conditions for hybridization include conditions that are generally used by persons skilled in the art to detect particular hybridization signals. Preferably, such conditions indicate stringent hybridization conditions and stringent washing conditions. Specifically, for instance, such conditions involve overnight incubation at 55° C. with the use of a probe in a solution containing 6×SSC (1×SSC composition: 0.15 M NaCl and 0.015 M sodium citrate (pH 7.0)), 0.5% SDS, 5×Denhardt's solution, and 100 mg/ml herring sperm DNA. Such conditions also involve washing of a filter in 0.2×SSC at 42° C. Stringent conditions involve a use of 0.1×SSC at 50° C. during a step of washing a filter. As a further stringent condition, a condition using 0.1×SSC at 65° C. during the same step can be explained.

The phrase "a DNA fragment comprising a DNA sequence comprising at least 20 consecutive bases of the nucleotide sequence set forth in SEQ ID NO: 3, 5, or 7 or of a sequence complementary to such nucleotide sequence" used herein indicates a DNA fragment obtained by choosing one or more sequence comprising at least 20 and preferably at least 30 (e.g., 40, 60, or 100) arbitrary consecutive bases of the sequence set forth in SEQ ID NO: 3, 5, or 7 in the Sequence Listing or of a sequence complementary to such sequence.

2. Production of a Recombinant DNA Having the Gene of the Protein

A recombinant DNA can be obtained by integrating the aforementioned DNA encoding DSA into a vector.

A vector that is appropriate for cloning is a vector that is constructed for gene recombination with the use of a phage or plasmid that is capable of autonomously replicating in a host microorganism. For instance, when *Escherichia coli* is a host microorganism, examples of such phage include Lambda gt10 and Lambda gt11. In addition, for instance, when *Escherichia coli* is a host microorganism, examples of such plasmid include pBTrp2, pBTac1, and pBTac2 (produced by Boehringer Mannheim), pKK233-2 (produced by Pharmacia), pSE280 (produced by Invitrogen), pGEMEX-1 (produced by Promega), pQE-8 (produced by QIAGEN), pQE-30 (produced by QIAGEN), pBluescriptII SK+ and pBluescriptII SK(−) (produced by Stratagene), pET-3 (produced by Novagen), pUC18 (produced by Takara Shuzo Co., Ltd.), pSTV28 (produced by Takara Shuzo Co., Ltd.), pSTV29 (produced by Takara Shuzo Co., Ltd.), and pUC118 (produced by Takara Shuzo Co., Ltd.).

As such promoter, any promoter may be used as long as it can be expressed in a host cell. Examples thereof include promoters derived from *Escherichia coli*, phages, or the like, such as a trp promoter ($P_{trp}$), a lac promoter ($P_{lac}$), a $P_L$ promoter, a $P_H$ promoter, and a $P_{SE}$ promoter. In addition, promoters and the like that are artificially designed and modified, such as a tac promoter and a lacT7 promoter, can be used. Further, in order to cause expression in bacteria of the genus *Bacillus*, it is also possible to use an Np promoter (JP Patent Publication (Kokoku) No. 8-24586 B (1996)).

As a ribosome binding sequence, any sequence can be used as long as it can be expressed in a host cell. However, it is preferable to use a plasmid in which a Shine-Dalgarno sequence and an initiation codon are adjusted to have an adequate distance (e.g., 6 to 18 bases) therebetween.

In order to efficiently carry out transcription and translation, a protein, in which the N-terminal of a protein having activity of the protein or a protein derived from such a protein by deletion of a portion thereof is fused with the N-terminal of a protein encoded by an expression vector, may be expressed.

A transcription termination sequence is not always necessary for the expression of a protein of interest. However, it is preferable to place a transcription termination sequence directly below a structural gene.

Upon cloning, it is possible to obtain a vector fragment by cleaving a vector as described above with a restriction enzyme used for cleavage of the aforementioned DNA encoding DSA. However, the same restriction enzyme used for cleavage of the DNA is not necessarily used. A method for binding the DNA fragment and a vector DNA fragment may be used as long as a known DNA ligase is used in such a method. For instance, after annealing of a cohesive end of the DNA fragment and that of a vector fragment, a recombinant vector of the DNA fragment and the vector DNA fragment is produced with the use of an adequate DNA ligase. Also, it is possible to produce a recombinant vector by transferring the resultant of such annealing into a host such as a microorganism and using an in vivo DNA ligase according to need.

3. Production of a Transformant Using a Recombinant DNA Constructed by Integrating DNA Encoding DSA into a Vector A transformant transformed with the aforementioned recombinant DNA can be obtained by introducing the aforementioned recombinant DNA into a host cell.

As a host cell, there is no particular limitation, as long as a recombinant vector is stable and can autonomously replicate and a foreign gene is phenotypically expressed therein. Examples of such host cell include microorganisms such as bacteria, including *Escherichia coli* such as *Escherichia coli* DH5α and *Escherichia coli* XL-1Blue. In addition, it is possible to use other microorganisms such as yeasts or insect cells as host cells.

In a case in which a microorganism is *Escherichia coli*, for example, the method for transferring recombinant DNA into the microorganism that can be used is a competent cell method using calcium treatment, an electroporation method, or the like.

As a host cell, for the purpose of restraining degradation of D-serine as a product, it is possible to use a microorganism having low D-serine deaminase activity or a microorganism lacking D-serine deaminase activity. Specific examples of a microorganism lacking D-serine deaminase activity include *Escherichia coli* having a recombinant D-serine deaminase gene described in Example 6.

In addition, for the purpose of restraining production of L-serine during a D-serine synthesis reaction, it is possible to degrade L-serine produced using a microorganism having high L-serine deaminase activity. As a microorganism having high L-serine deaminase activity, *Escherichia coli* having a recombinant L-serine deaminase gene described in Example 15 or the like can be used.

As such microorganism, a microorganism having low activity of an enzyme involved in L-serine synthesis, such as alanine racemase, serine hydroxymethyltransferase, or L-threonine aldolase, or a microorganism lacking such enzyme activity is preferably used so that L-serine is not produced.

Further preferably, a microorganism lacking all of the above enzymes is used as a host cell.

4. Production of DSA

DSA can be produced by culturing the aforementioned transformant and collecting the thus obtained DSA.

A transformant can be cultured in accordance with a usual method used for culture of host cells. In a case in which a transformant is a procaryotic microorganism such as *Escherichia coli* or a eucaryotic microorganism such as a yeast, a medium in which such a microorganism is cultured may be a natural or synthetic medium as long as it contains carbon sources, nitrogen sources, inorganic salts, and the like, which cause assimilation of the microorganism, and as long as a transformant can efficiently be cultured therein.

Examples of carbon sources that can be used include: glucose, fructose, or sucrose; molasses containing any thereof; carbohydrates such as starch and starch hydrolysate; organic acids such as acetic acid and propionic acid; and alcohols such as ethanol and propanol, as long as they can cause assimilation of a transformant.

Examples of nitrogen sources that can be used include: ammonia; a variety of ammonium salts of inorganic or organic acid, such as ammonium chloride, ammonium sulfate, ammonium acetate, and ammonium phosphate; other nitrogen-containing compounds; peptone; meat extracts; yeast extracts; corn steep liquor; casein hydrolysate; soybean cake; soybean cake hydrolysate; and a variety of fermentation bacteria and digests thereof.

Examples of inorganic salts that can be used include monopotassium phosphate, dipotassium phosphate, magnesium phosphate, magnesium sulfate, sodium chloride, ferrous sulfate, manganese sulfate, copper sulfate, and calcium carbonate.

Culture is carried out under aerobic conditions used for shake culture, submerged cultivation under aeration and agitation, or the like. Culture temperature is preferably 15° C. to 50° C. Culture time is 16 hours to 5 days, in general. During culture, pH is maintained between 3.0 and 9.0. The pH is adjusted with the use of inorganic or organic acids, alkaline solutions, urea, calcium carbonate, ammonia, and the like. In addition, during culture, antibiotics such as ampicillin and tetracycline may be added to the medium according to need.

When a microorganism transformed with an expression vector in which an inducible promoter is used as a promoter is cultured, an inducer may be added to the medium according to need. For instance, when a microorganism transformed with an expression vector in which a lac promoter is used is cultured, isopropyl-β-D-thiogalactopyranoside (IPTG) or the like may be added to the medium. Also, when a microorganism transformed with an expression vector in which a trp promoter is used is cultured, indoleacetic acid (IAA) or the like may be added to the medium.

A transformant can be separated and recovered by means of centrifugation, filtration, or the like, of a culture solution containing the transformant.

A treated product of a transformant can be obtained by allowing the transformant to be subjected to mechanical disruption, ultrasonication, freezing and thawing treatment, drying treatment, pressurization or depressurization treatment, osmotic pressure treatment, autodigestion, surfactant treatment, or enzyme treatment for the purpose of cell disruption. Also, a treated product of a transformant can be obtained as an immobilized fraction or transformant, which comprises DSA obtained via such treatment.

In addition, the treated product of a microorganism of the present invention is also referred to as a product subjected to a treatment similar to that used for the aforementioned treated product of a transformant.

In order to purify DSA from such transformant or a treated product of such transformant, transformed cells are disrupted and a cell disruption solution is subjected to a combination of, for example, fractionation via ion-exchange resin or gel-filtration chromatography or the like and salting out with the use of ammonium sulfate or the like, such that a purified enzyme can be obtained.

5. Production of D-Serine

D-serine can be produced by allowing glycine to react with formaldehyde in the presence of the aforementioned transformant or a treated product of the transformant.

Production of D-serine is preferably carried out under conditions of shaking or agitation at pH 6.0 to 9.0 and at a temperature of 20° C. to 60° C.

The amount of transformant or treated product of the transformant used is not particularly limited, as long as the reaction between formaldehyde and glycine progresses well. In general, a transformant or a treated product of the transformant is preferably added in an amount of at least 10 units and preferably 50 units or more in terms of DSA activity relative to 1 g of glycine. In accordance with a method for adding the transformant or a treated product of the transformant, such transformant may be added at once upon the initiation of reaction, at several different times, or continuously throughout reaction.

Regarding DSA activity, capacity for synthesizing 1 μmol of D-serine per 1 minute is defined as 1 unit.

DSA activity is calculated by measuring the amount of D-serine that is produced in a manner such that an enzyme solution is added to 200 mM Tris-hydrochloric acid buffer (pH 8.0) containing 100 mM glycine, 0.1 mM pyridoxal phosphate, 10 mM magnesium chloride, and 5 mM formaldehyde, followed by incubation at 30° C.

Glycine concentration in a reaction solution is 100 mM or more and preferably between 1 M and 5 M. In accordance with a method for adding glycine, it may be added at once upon the initiation of reaction, at several different times, or continuously along with the progress of reaction.

It is possible to supply formaldehyde in the form of gas into a reaction solution. Also, it can be supplied in the form of an aqueous or alcohol solution. In addition, as a supply source of formaldehyde, paraformaldehyde can also be used. However, an aqueous solution of approximately 37% formaldehyde is preferably used.

As a method for adding formaldehyde, a method of adding formaldehyde at once or a method of adding formaldehyde at several different times or continuously along with the progress of reaction can be carried out. Preferably, formaldehyde concentration in a reaction solution is controlled at a concentration that allows DSA activity not to be inhibited. A concentration that allows DSA activity not to be inhibited is generally 5 M or less, preferably 2 M or less, further preferably 500 mM or less, and particularly preferably 300 mM or less.

Also, formaldehyde can be added by the following methods for controlling formaldehyde concentration in a reaction solution: (1) a method for adding formaldehyde in a reaction solution at a given rate; (2) a method wherein formaldehyde concentration is quantified such that formaldehyde is added at several different times at a concentration that allows enzyme activity not to be deactivated; (3) a method for substantially avoiding inhibition due to formaldehyde, wherein paraformaldehyde is added and an enzyme is added to a reaction system at a rate that exceeds the rate at which formaldehyde is released from paraformaldehyde; and (4) a method for adding formaldehyde in an amount at which an increased pH level can be corrected. In the case of (4) above, D-serine as a product accumulates in a reaction solution along with the progress of reaction, the amount of glycine as a starting material decreases, and the pH of a reaction solution decreases along with the progress of the reaction. This is because the isoelectric point of D-serine is 5.68 and that of glycine is 5.97, such that alkali is added to the reaction solution in an amount that exceeds an amount necessary for correction of a decrease in the pH of the reaction solution, resulting in an increased pH level.

When formaldehyde is added at a rate that exceeds the rate of adding alkali while the amount of DSA in a reaction solution is predetermined (that is to say, at a rate that exceeds the rate of D-serine synthesis), it becomes possible to control formaldehyde concentration in a reaction solution without using complicated operations such as measurement of formaldehyde concentration.

Examples of alkali that may be added to a reaction solution include: alkali metal hydroxide such as lithium hydroxide, sodium hydroxide, or potassium hydroxide; ammonium hydroxide; calcium hydroxide; dipotassium phosphate; disodium phosphate; potassium pyrophosphate; and ammonia, as long as it is dissolved in water such that basicity is imparted to the liquid.

A medium used for a reaction solution is water, an aqueous medium, an organic solvent, or a mixture solution of water or an aqueous medium and an organic solvent. Examples of an aqueous medium that is used include buffer solutions such as a phosphate buffer solution, a HEPES (N-2-hydroxyethylpiperazin-N-ethanesulfonic acid) buffer solution, and a Tris (Tris(hydroxymethyl)aminomethane) hydrochloric acid buffer solution. Examples of an organic solvent that may be used include any organic solvent such as acetone, ethyl acetate, dimethyl sulfoxide, xylene, methanol, ethanol, or butanol, unless it inhibits reaction.

In the aforementioned reaction, reaction yield may be improved with the addition of a compound having divalent metal ions, reductants such as 2-mercaptoethanol, dithiothreitol, and sodium bisulfite, and coenzymes such as pyridoxal phosphate and an ammonium salt.

Examples of a compound having divalent metal ions include magnesium chloride, manganese chloride, cobalt acetate, ferrous sulfate, and calcium chloride.

The concentration of such compound in a reaction solution is generally 0.1 mM to 100 mM and preferably 0.1 mM to 10 mM.

6. Method for Improving Optical Purity of D-Serine in a Reaction Solution

Formation of L-serine as a byproduct can be restrained by allowing glycine to react with formaldehyde in the presence of a treated product obtained by allowing the aforementioned transformant or a treated product of the transformant to be subjected to heat treatment or in the presence of a treated product obtained by allowing the aforementioned transformant or a treated product of the transformant to be subjected to organic solvent treatment.

As conditions of heat treatment, any conditions may be applied, provided that thereby DSA activity is not significantly reduced by heating and L-serin production activity can be reduced or eliminated. Specific examples of such treatment include a method of agitation at pH 6.0 to 9.0 at a temperature of 40° C. to 70° C. for 10 minutes to 6 hours.

In addition, organic solvent treatment and heat treatment can be used in combination.

As conditions of organic solvent treatment, any conditions may be applied, provided that thereby DSA activity is not significantly reduced and L-serin production activity can be reduced or eliminated. Such conditions of organic solvent treatment involve organic solvent concentration that is generally approximately between 20 mM and 2 M, preferably approximately between 20 mM and 1 M, further preferably approximately between 50 mM and 1000 mM, and particularly preferably approximately between 50 mM and 300 mM. Preferred examples of an organic solvent that is used include: aldehydes such as formaldehyde, acetaldehyde, and benzaldehyde; alcohols such as methanol, ethanol, and isopropyl alcohol; ketones such as acetone; and halogenated hydrocarbons such as dichloroethane. However, the organic solvent is not limited thereto unless it causes a significant decrease in DSA activity. Among them, formaldehyde is the most preferable because it is a substrate for enzyme reactions. Since the addition of D-serine results in production of formaldehyde during such enzyme reaction, a method for adding D-serine instead of formaldehyde may be implemented. It is desired that the concentration of D-serine added be approximately 100 mM to 5 M.

It is desired that the temperature for organic solvent treatment be between 10° C. and 50° C. and that the pH for the treatment be between 6.0 and 9.0. During organic solvent treatment, agitation is desirably carried out such that the pH and the organic solvent concentration become uniform in a treatment solution.

In addition, upon the initiation of reaction of D-serine production, it is possible to reduce or deactivate L-serine production activity by increasing formaldehyde concentration. In such case, formaldehyde concentration during reaction is maintained at approximately 0.1% to 5% for 30 minutes to 3 hours and then a general reaction may be carried out.

When carrying out the aforementioned treatment, enzyme activity may be further stabilized by adding a compound having divalent metal ions, reductants such as 2-mercaptoethanol, dithiothreitol, and sodium bisulfite, and coenzymes such as pyridoxal phosphate and an ammonium salt.

Examples of a compound having divalent metal ions include magnesium chloride, manganese chloride, cobalt acetate, ferrous sulfate, and calcium chloride.

A concentration of such compound in a treatment solution is generally 0.1 mM to 100 mM and preferably 0.1 mM to 10 mM.

It is also possible to improve optical purity of D-serine as a final product by adding L-serine-deaminase-producing bacteria to a reaction solution after the termination of a D-serine synthesis reaction so as to degrade the L-serine produced. As L-serine deaminase-producing bacteria, microorganisms lacking D-serine deaminase are desirably used.

7. Method for Collecting D-Serine

D-serine can be collected from a reaction solution in accordance with methods that are used in general organic synthetic chemistry, such as extraction using organic solvents, crystallization, thin-layer chromatography, and high-performance liquid chromatography.

In accordance with the present invention, D-serine can be produced from glycine and formaldehyde with a better yield than is possible with methods for producing D-serine using known DTAs.

Figure 1:
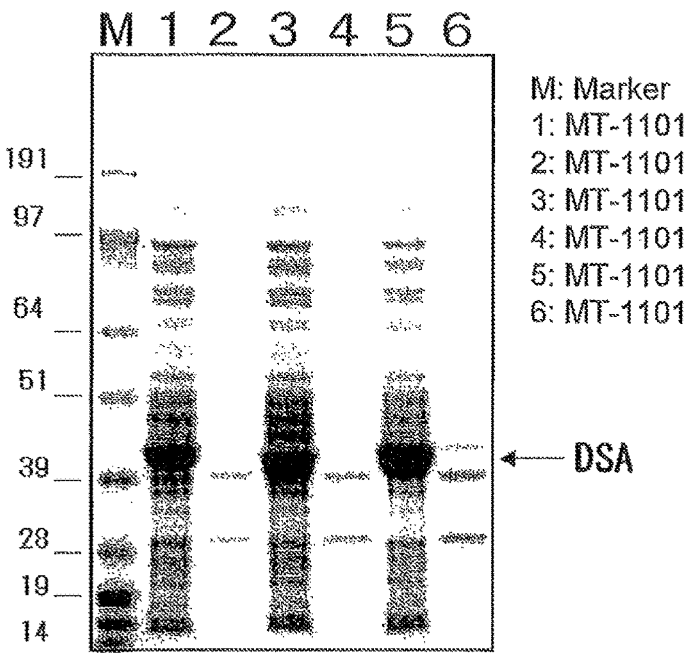
FIG. 1 shows the results of SDS-polyacrylamide gel electrophoresis analysis of a cell disruption solution obtained from transformants.

This description includes part or all of the contents as disclosed in the description and/or drawings of Japanese Patent Application No. 2004-298344, which is a priority document of the present application.

BEST MODE FOR CARRYING OUT THE INVENTION

Examples of the present invention will hereafter be described. However, the technical scope of the present invention is not limited to the Examples. In addition, D-serine, L-serine, and glycine were quantified by high-performance liquid chromatography. Conditions for analyzing them and a method for measuring activities of enzymes (DSA and DTA) were as follows.

(1) Conditions for Analyzing D-Serine and L-Serine

Column: TSK-GEL ENANTIO L1 4.6×250 (Tosoh Corporation)

Column temperature: 45° C.

Pump flow rate: 0.8 ml/min.

Detection: UV 254 nm

Eluent: 0.25 mM copper sulfate:methanol=9:1 (v/v)

(2) Conditions for Analyzing Serine and Glycine

Column: Shodex RSpak NN-814 8×250 (Showa Denko K.K.)

Column temperature: 40° C.

Eluent: 10 mM potassium phosphate (pH 3.0)

Pump flow rate: 0.8 ml/min

Detection was carried out by a post-column derivatization method (J. Chromatogr., 83, 353-355 (1973)) using orthophthalaldehyde (OPA).

(3) a Method for Measuring Enzyme Activity

An enzyme solution that had been obtained by allowing a cell suspension to be subjected to ultrasonic disruption was adequately diluted. The diluted enzyme solution (0.1 mL) was added to 0.9 mL of 200 mM Tris-hydrochloric acid buffer (pH 8.0) containing 100 mM glycine, 0.1 mM pyridoxal phosphate, 10 mM magnesium chloride, and 5 mM formaldehyde. The resulting solution was subjected to reaction at 30° C. for 15 minutes.

D-serine produced was analyzed by HPLC so as to measure the activity.

Herein, 1 unit of such activity was determined to be the capacity for producing 1 μmol of D-serine per 1 minute.

Example 1

(Obtaining the Gene Encoding DSA)

An LB medium (50 ml) was inoculated with *Achromobacter xylosoxidans* (ATCC9220), *Achromobacter denitrificans* (NBRC15125), and *Achromobacter xylosoxidans* (NBRC13495). After overnight culture at 30° C., harvest was carried out, followed by bacteriolysis using a lytic solution containing lysozyme (1 mg/ml). The resulting lysate was subjected to phenol treatment. Then, DNA was allowed to precipitate by ethanol precipitation in accordance with a usual method. The resulting DNA precipitate was recovered by spooling it onto a glass rod and washed so as to be used for PCR.

Primers used for PCR were oligonucleotides (obtained by custom synthesis from Hokkaido System Science Co., Ltd.) having the nucleotide sequences set forth in SEQ ID NOS: 1 and 2, respectively, which were designed based on known DTA genes. These primers had KpnI and HindIII restriction enzyme recognition sequences near the 5' and 3' ends, respectively.

With the use of 0.025 ml of a PCR reaction solution containing 6 ng/μl each of chromosome DNAs of the aforementioned microorganisms and 3 μM each of the primers, PCR was carried out under the following conditions: denaturation at 96° C. for 1 minute, annealing at 55° C. for 30 seconds, and elongation reaction at 68° C. for 1 minute and 15 seconds for 35 reaction cycles.

The PCR reaction product and plasmid pUC18 (Takara Shuzo) were digested with KpnI and HindIII, followed by ligation using Ligation High (TOYOBO). Thereafter, the obtained recombinant plasmid was used for transformation of *Escherichia coli* DH5α. The transformed cell line was cultured in an LB agar medium containing 50 μg/ml of ampicillin (Am) and X-Gal (5-bromo-4-chloro-3-indolyl-β-D-galactoside). Thus, an Am-resistant transformed cell line that was formed into a white colony was obtained. A plasmid was extracted from the thus obtained transformed cell line. The nucleotide sequence of the DNA fragment that had been introduced into the plasmid was confirmed in accordance with a usual method for base sequencing.

Molecular weights of amino acid sequences that were expected based on the obtained DNAs encoding DSA were approximately 40 kDa each.

The obtained plasmid having DNA encoding DSA derived from *Achromobacter xylosoxidans* (ATCC9220) was designated as pAcDTA1.

The plasmid having DNA encoding DSA derived from *Achromobacter xylosoxidans* (NBRC13495) was designated as pAcDTA2. The plasmid having DNA encoding DSA derived from *Achromobacter denitrificans* (NBRC15125) was designated as pAcDTA3.

(Production of Transformants)

*Escherichia coli* DH5α was transformed by a usual method using pAcDTA1, pAcDTA2, and pAcDTA3. The obtained transformants were designated as MT-11015, MT-11016, and MT-11017, respectively.

A LB medium (100 mL) containing 50 μg/ml of Am was inoculated with recombinant microorganisms of each transformant after being placed in a 500-mL baffled Erlenmeyer flask. This was followed by culture at 30° C. until OD660 reached 0.6. Then, IPTG (isopropyl-β-thiogalactopyranoside) was added thereto such that the medium contained 1 mM IPTG. This was followed by further shake culture for 16 hours. The culture solution was centrifuged at 13000 rpm for 10 minutes. The obtained cell bodies were suspended in 100 mM Tris-hydrochloric acid buffer (pH 8.0) containing 5 mL of 1 mM magnesium chloride, followed by cryopreservation at −20° C.

Example 2

(Method for Producing DSA)

Suspensions (0.5 mL each) of the transformants produced in Example 1 were disrupted using a Bioruptor (produced by Olympus) in ice water for 5 minutes. A transformant disruption solution was centrifuged such that the transformant disruption solution was prepared. FIG. 1 shows the results of SDS-polyacrylamide gel electrophoresis analysis of the transformant disruption solution.

0.5 mL of 100 mM Tris-hydrochloric acid buffer (pH 8.0) was added to the precipitate so as to obtain cell residue, followed by analysis in a similar manner.

In a soluble fraction of each transformant, a protein that was expressed at a position of 40 kDa was found. However, such protein was not found in an insoluble fraction. The molecular weight of the protein was almost equivalent to the molecular weight of an amino acid sequence that was based on the corresponding gene.

Example 3

(Purification of DSA and D-Serine Synthesis with the Use of Purified DSA)

10 mL of a MT-11015 disruption solution produced in a manner similar to that used in Example 2 was centrifuged at 10000 rpm for 20 minutes such that an enzyme solution was prepared, and cell residue was then removed therefrom. The enzyme solution was allowed to adsorb anion exchange resin (HiTrap Q-XL produced by Amersham), followed by linear-gradient elution from 100 mM Tris-hydrochloric acid buffer (pH 8.0) containing 10 mM magnesium chloride and 50 mM sodium chloride to 100 mM Tris-hydrochloric acid buffer (pH 8.0) containing 10 mM magnesium chloride and 500 mM sodium chloride. The activity fraction was allowed to adsorb hydrophobic chromatography resin (HiTrap Phenyl FF produced by Amersham), followed by linear-gradient elution from 100 mM Tris-hydrochloric acid buffer (pH 8.0) containing 10 mM magnesium chloride, which had been saturated with ammonium sulfate, to 100 mM Tris-hydrochloric acid buffer (pH 8.0) containing 10 mM magnesium chloride. Note that the above operations were carried out at approximately 10° C.

Figure 2:
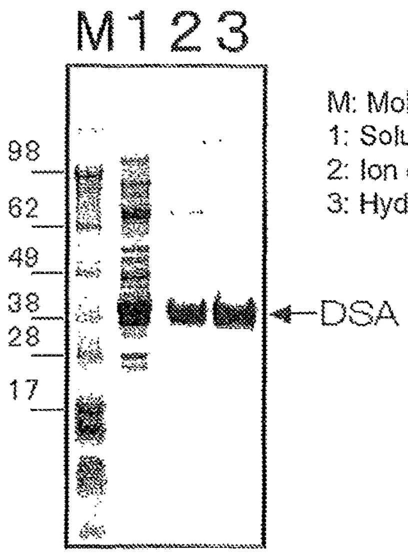
FIG. 2 shows an SDS-polyacrylamide gel electrophoresis image of purified DSA.

FIG. 2 shows the results of SDS-polyacrylamide gel electrophoresis analysis of a solution subjected to ultrasonic disruption, an activity fraction subjected to ion-exchange chromatography treatment, and an activity fraction subjected to hydrophobic chromatography treatment. The molecular weight of purified DSA monomer was 40000±5000.

The purified DSA enzyme solution (150 units) was added to a substrate solution comprising 100 mM formaldehyde, 100 mM glycine, 0.1 mM PLP, 10 mM magnesium chloride, and 100 mL of 200 mM Tris-hydrochloric acid buffer (pH 8.0). The resultant was subjected to reaction at 30° C. for 20 hours.

The reaction yield of D-serine was 95%.

Example 4

(Comparison Between D-Serine Synthesis Capacity and D-Threonine Synthesis Capacity)

The enzyme solution subjected to ultrasonic disruption (150 units) of the cell line MT-11015 produced in Example 1 was added to a substrate solution comprising 100 mM formaldehyde or acetaldehyde as an aldehyde source, 100 mM glycine, 0.1 mM PLP, 10 mM magnesium chloride, and 100 mL of 200 mM Tris-hydrochloric acid buffer (pH 8.0). The resultant was subjected to reaction at 30° C. for 20 hours.

When formaldehyde was used as an aldehyde source, the yield was 90%. Also, when acetaldehyde was used as aldehyde source, the yield was 10%.

Example 5

(D-Serine Synthesis Reaction at a Formaldehyde Concentration of 100 mM)

The enzyme solutions (150 units each) subjected to ultrasonic disruption of the recombinant microorganisms produced in Example 1 were separately added to a substrate solution comprising 100 mL of 200 mM Tris-hydrochloric acid buffer (pH 8.0) containing 100 mM formaldehyde, 100 mM glycine, 0.1 mM PLP, and 10 mM magnesium chloride. The resultants were subjected to reaction at 30° C. for 20 hours. Table 1 shows the results

TABLE 1

| Host | Plasmid | Reaction yield |
|---|---|---|
| DH5α | pAcDTA1 | 90% |
| | pAcDTA2 | 80% |
| | pAcDTA3 | 72% |

Example 6

(Production of D-Serine Deaminase-Deficient *Escherichia coli*)

The entire nucleotide sequence (GenBanak accession number: U00096) of genomic DNA of *Escherichia coli* is known to the public. Also, the amino acid sequence of *Escherichia coli* D-serine deaminase and the nucleotide sequence (GenBank accession number: J01603) of the gene thereof (hereafter to be abbreviated in some cases as dsdA) have already been reported. PCR was carried out using genomic DNA of *Escherichia coli* cell line W3110 (ATCC27325) as a template and oligonucleotides having the nucleotide sequences set forth in SEQ ID NOS: 9, 10, 11, and 12, which had been produced based on genetic information regarding a region in the vicinity of dsdA of genomic DNA of *Escherichia coli* cell line W3110. The obtained DNA fragments were digested with PstI and XbaI and with XbaI and KpnI, respectively, which are restriction enzymes. Thus, approximately 900-bp and 800-bp fragments of each DNA fragment were obtained. The resulting DNA fragments were mixed with fragments obtained by digesting a temperature-sensitive cloning vector pTH18cs1 (GenBank accession number: AB019610) (Hashimoto-Gotoh, T., Gene, 241, 185-191 (2000)) with PstI and KpnI, followed by ligation using a ligase. The resultant was transformed into a DH5α cell line at 30° C. Thus, a transformant that was able to grow on an LB agar plate containing 10 μg/ml of chloramphenicol was obtained. The obtained colony was cultured overnight at 30° C. in an LB liquid medium containing 10 μg/ml of chloramphenicol so that a plasmid was recovered from the obtained cell bodies. The obtained plasmid was digested with XbaI so as to be subjected to blunt-end treatment with T4DNA polymerase. Thereafter, the plasmid was ligated with a kanamycin-resistant gene derived from pUC4K plasmid (Pharmacia).

The thus obtained plasmid was transformed into *Escherichia coli* cell line W3110 (ATCC27325) at 30° C., followed by overnight culture at 30° C. on an LB agar plate containing 10 μg/ml of chloramphenicol and 50 μg/ml of kanamycin. Thus, a transformant was obtained. An LB liquid medium containing 50 μg/ml of kanamycin was inoculated with the obtained transformant, followed by overnight culture at 30° C. Next, the resultant was applied to an LB agar plate containing 50 μg/ml of kanamycin so as to obtain the culture cell bodies. Thus, colonies that were able to grow at 42° C. were obtained. The obtained colonies were cultured overnight at 30° C. in an LB liquid medium containing 50 μg/ml of kanamycin. The resultant was further applied to an LB agar plate containing 50 μg/ml of kanamycin so as to obtain colonies that were able to grow at 42° C.

100 colonies were randomly picked up from the colonies that appeared. Each of them was allowed to grow on an LB agar plate containing 50 μg/ml of kanamycin and on an LB agar plate containing 10 μg/ml of chloramphenicol. Then, chloramphenicol-sensitive clones that exclusively grow on an LB agar plate containing kanamycin were selected. Further, fragments (of approximately 3.0 kb) in the region in the vicinity of dsdA were amplified by PCR from chromosome DNAs of these clones of interest. Then, a cell line in which dsdA had been substituted with a kanamycin-resistant gene was selected. The obtained cell line was designated as a W3110dsdA-deficient cell line (hereafter to be abbreviated in some cases as ΔdsdA). Transformation was carried out using the plasmids produced in Example 1 so that cryopreservated cell bodies were produced as described above. Then, a similar reaction was carried out. As a result, substantially no D-serine degradation was confirmed.

Example 7

(Production of D-Serine with the Use of a Transformant MT-11016: Production without Addition of Mg)

Distilled water (53.1 g) was added to 7.5 g of glycine and 9.4 g of pyridoxal phosphate (0.026% by weight). The resultant was adjusted to pH 8.0 with sodium hydroxide. A cell suspension (corresponding to 1500 units in terms of activity) of MT-1016 obtained in Example 1 was added thereto. Then, 20.8 g of formaldehyde (20% by weight) was added thereto at a reaction temperature of 30° C. in a manner such that formaldehyde concentration in the reaction solution was quantified by the AHMT method (Eisei Kagaku (Journal of Health Science) (1976), Vol. 22, p. 39) as being between 50 mM and 300 mM. The pH of the reaction solution was adjusted to pH 8.0 with sodium hydroxide. The reaction yield after 72 hours reached 85%.

Example 8

(Production of D-Serine with the Use of a Transformant MT-11017: Production without Addition of Mg)

Distilled water (53.1 g) was added to 7.5 g of glycine and 9.4 g of pyridoxal phosphate (0.026% by weight). The resultant was adjusted to pH 8.0 with sodium hydroxide. A cell suspension (corresponding to 1500 units in terms of activity) of MT-11017 obtained in Example 1 was added thereto. Then, 20.8 g of formaldehyde (20% by weight) was added to the reaction solution at a reaction temperature of 30° C. by repeating cycles of addition of formaldehyde at a rate of 0.8 g/15 minutes for 15 minutes and discontinuation of the addition of formaldehyde for 45 minutes. The pH of the reaction solution was adjusted to pH 8.0 with sodium hydroxide during reaction. After 24 hours, the reaction yield of D-serine reached 95%.

Meanwhile, when formaldehyde was added at once so as to be subjected to reaction, the reaction yield was 20%.

Example 9

(Production of D-Serine with the Use of a Transformant Treated with Formaldehyde: Production without Addition of Mg)

Formaldehyde was added to a lysate of the frozen cell bodies of MT-11015 produced in Example 1 such that the lysate contained 100 mM formaldehyde, followed by mild agitation at 30° C. for 1 hour. During agitation, the pH was adjusted to 8.0 with sodium hydroxide. The resulting suspension of the cell bodies was subjected to the same reaction as that of Example 8. When formaldehyde treatment was not carried out, 2 mol % of L-serine was produced. When formaldehyde treatment was carried out, it was impossible to detect L-serine.

6N-hydrochloric acid was added to the above reaction solution such that the solution was adjusted to pH 4.1. Activated carbon (0.97 g; water content of 50%) was added thereto, followed by agitation at 60° C. for 1 hour. Activated carbon and cell body components were removed by filtration. Then, the filtrate was concentrated to 30 g. Isopropyl alcohol (13 g) was gradually added thereto, followed by mild agitation on ice for 1 hour. Thus, D-serine was allowed to deposit. The solution containing crystal deposits was filtrated. The crystal deposits were washed with 13 mL of cooled 40% isopropyl alcohol, followed by dehydration. The recovery rate was 60%, and white D-serine crystal was obtained. Glycine as a starting material was not detected. The optical purity of the crystal was 99.8% ee.

Example 10

[10-1] (Cloning of DTA of *Xanthomonas* and Vector Construction)

An LB medium (50 ml) was inoculated with *Xanthomonas oryzae* (IAM1657), which is obtainable from the Institute of Molecular and Cellular Biosciences at the University of Tokyo. After overnight culture at 30° C., harvest was carried out, followed by bacteriolysis using a lytic solution containing lysozyme (1 mg/ml). The resulting lysate was subjected to phenol treatment. Then, DNA was allowed to precipitate by ethanol precipitation in accordance with a usual method. The resulting DNA precipitate was recovered by spooling it onto a glass rod and washed so as to be used for PCR.

Primers used for PCR were oligonucleotides (obtained by custom synthesis from Hokkaido System Science Co., Ltd.) having the nucleotide sequences set forth in SEQ ID NOS: 13 and 14, respectively, which were designed based on a known DTA gene of *Xanthomonas oryzae* (GenBanak accession number: E05055). These primers had KpnI and HindIII restriction enzyme recognition sequences near the 5' and 3' ends, respectively.

With the use of 0.025 ml of a PCR reaction solution containing 6 ng/μl each of chromosome DNAs of the aforementioned microorganisms and 3 μM each of the aforementioned primers, PCR was carried out under the following conditions: denaturation at 96° C. for 1 minute, annealing at 55° C. for 30 seconds, and elongation reaction at 68° C. for 1 minute and 15 seconds for 35 reaction cycles.

The PCR reaction product and plasmid pUC18 (Takara Shuzo) were digested with KpnI and HindIII, followed by ligation using Ligation High (TOYOBO). Thereafter, the obtained recombinant plasmid was used for transformation of *Escherichia coli* DH5α. The transformed cell line was cultured in an LB agar medium containing 50 μg/ml of ampicillin (Am) and X-Gal (5-bromo-4-chloro-3-indolyl-β-D-galactoside). Thus, an Am-resistant transformed cell line that was formed into a white colony was obtained. A plasmid was extracted from the thus obtained transformed cell line. The nucleotide sequence of the DNA fragment that had been introduced into the plasmid was confirmed to be a sequence identical to the sequence of DTA of *Xanthomonas oryzae* in accordance with a usual method for base sequencing. The obtained expression plasmid was designated as pXDTA1.

[10-2] (Obtaining *Escherichia coli* Expressing DTA of the Genus *Xanthomonas*)

*Escherichia coli* W3110ΔdsdA was transformed by a usual method using pXDTA1. The obtained transformed cell line was designated as MT-11028.

In addition, *Escherichia coli* W3110ΔdsdA was transformed by a usual method using pAcDTA1, pAcDTA2, and pAcDTA3 obtained in Example 1. The obtained transformants were designated as MT-11015W, MT-11016W, and MT-11017W, respectively.

[10-3] (Obtaining Cell Bodies Via Jar Culture)

A LB medium (100 mL) containing 50 μg/ml of Am was inoculated with recombinant *Escherichia coli* (MT-11015W, MT-11016W, MT-11017W, and MT-11028) after being placed in a 500-mL baffled Erlenmeyer flask. This was followed by culture at 30° C. until OD660 reached 1.0.

Subsequently, culture was carried out using BMS10 with capacity of 10 L (produced by ABLE). Operations were carried out under the following culture conditions: agitation: 700 rpm; temperature: 30° C.; pH (maintained with $NH_3$): 7.2; aeration: 1 vvm; capacity: 5 L; and culture time: 48 hours. A medium used had a medium composition comprising 7 g of polypeptone (Dainippon Pharma), 0.09 g of ferrous sulfate heptahydrate, 1.5 g of ammonium sulfate, 2 g of magnesium sulfate hexahydrate, 2 g of monopotassium hydrogen phosphate, 2 g of dipotassium hydrogen phosphate, and 0.6 g of ADEKA NOL LG126 (Asahi Denka Kogyo K.K.) with respect to 1 L of water, unless specified.

Before inoculation, glucose was added, resulting in a glucose concentration of 20 g/L. Then, 50 mL of the culture solution in the aforementioned baffled Erlenmeyer flask was used for inoculation. After the glucose that had been added first became depleted under the aforementioned conditions, glucose was supplied at a variable rate (that resulted in less than 0.1 g/L of glucose) during the remaining time such that the total amount of glucose added was 200 g. Cell bodies were collected from the culture solution via centrifugation so as to be frozen at −20° C.

[10-4] (Restraining of Formation of L-Serine as a Byproduct from a Microorganism Treated with an Organic Solvent)

[Method for Measuring Enzyme Activity of Formation of L-Serine as a Byproduct]

Magnesium chloride hexahydrate (1.0 g) was added to 60 g of frozen cell bodies of MT-11028 (with a solid content percentage of approximately 10%). A variety of organic solvents were added thereto in a manner such that the resultant contained the solvents at given concentrations, followed by agitation at 35° C. for 1 hour.

Cell bodies (weighing 0.22 g as dry cell bodies) were taken from the above processed cell solution. The solution (9 g) used for enzyme activity measurement was added thereto, followed by agitation at 35° C. for 20 hours. Then, the ratio between L-serine produced and residual D-serine was measured. Table 2 collectively shows the results.

(Solution Used for L-Serine Production Activity Measurement) D-serine (10.84 g) and PLP (6 mg) were dissolved in 0.5 M potassium phosphate buffer (pH 7.0) such that 100 g of the resultant was obtained.

TABLE 2

| Type of organic solvent | Concentration upon treatment | Optical purity of D-serine | DSA residual activity |
|---|---|---|---|
| Water | | 93% | 95% |
| Isopropyl alcohol | 20% by weight | 96% | 50% |
| Benzaldehyde | 5% by weight | 97.5% | 82% |
| Dichloroethane | 5% by weight | 98.2% | 103% |
| Formaldehyde | 0.5% by weight | 98.7% | 46% |

Example 11

(D-Serine Synthesis with the Use of Microorganisms Treated with an Organic Solvent)

Magnesium chloride hexahydrate (1.85 g) and 1.2 g of formaldehyde (37% by weight) were added to 83.4 g of wet cell bodies (with a solid content percentage of approximately 10%) obtained in Example 10. Water was added thereto such that the formaldehyde concentration was adjusted to 0.5%, followed by agitation at 35° C. for 1 hour.

Glycine (80 g), 4 g of magnesium chloride hexahydrate (35% by weight), and 3.1 g of formaldehyde (37% by weight) were added to 280 g of water. The pH of the resultant was adjusted to 7.5 with sodium hydroxide.

3.2 g of a PLP solution (0.38% by weight) was added thereto. Reaction was initiated by adding 30 g of the above cell bodies treated with an organic solvent as wet cell bodies. During reaction, formaldehyde was added when the pH became higher than 7.3 so that the pH was controlled at 7.3. The formaldehyde concentration during reaction was obtained by subtracting the amount of D-serine produced that was quantified by HPLC from the amount of formaldehyde added. The formaldehyde concentration in the reaction solution was controlled approximately between 80 mM and 100 mM. As a result of analysis of serine after the termination of reaction by HPLC, the yield relative to that of Gly was 95 mol % and the optical purity was 99.9% ee.

Example 12

(Example of Reaction with High Formaldehyde Concentration)

Glycine (80 g) and 4 g of magnesium chloride hexahydrate (35% by weight) were added to 280 g of water so as to be dissolved therein. Formaldehyde was added thereto such that the concentrations listed below were achieved, followed by control of pH at 7.5 with the use of sodium hydroxide. After the addition of 3.2 g of PLP (0.38% by weight), 30 g of frozen cell bodies obtained in Example 10 were added thereto so as to initiate reaction. When the pH reached 7.3 or more during reaction, formaldehyde was added such that pH was controlled at 7.3. Table 3 collectively shows the results.

TABLE 3

| | Micro-organism | Formaldehyde concentration in reaction solution | Optical purity | Reaction yield |
|---|---|---|---|---|
| Comparative example | MT-11028 | 10 to 20 mM | 96.5% | 77.9% |
| Examples | MT-11028 | Approximately 150 mM | 98.1% | 98.0% |
| | | Approximately 330 mM | 99.8% | 98.5% |
| | | Approximately 410 mM | 99.9% | 96.6% |
| | | Approximately 660 mM | 99.9% | 95.0% |
| | | Approximately 1300 mM | 99.9% | 95.0% |
| | | Approximately 2000 mM | 99.9% | 90.0% |
| | MT-11015W | Approximately 410 mM | 99.9% | 89.7% |
| | MT-11016W | Approximately 410 mM | 99.8% | 96.6% |
| | MT-11017W | Approximately 410 mM | 99.8% | 90.5% |

Example 13

[13-1] (Construction of *Escherichia coli* in which the glyA Gene is Destroyed and Production of DSA-Producing Bacteria)

The entire nucleotide sequence of *Escherichia coli* genomic DNA is known to the public (GenBanak accession number: U00096). Also, the amino acid sequence of *Escherichia coli* serine hydroxymethyltransferase and the nucleotide sequence (GenBank accession number: J01620) of the gene thereof (hereafter to be abbreviated in some cases as glyA) have already been reported. PCR was carried out using genomic DNA of *Escherichia coli* cell line W3110 (ATCC27325) as a template and oligonucleotides having the nucleotide sequences set forth in SEQ ID NOS: 15, 16, 17, and 18, which were produced based on genetic information regarding a region in the vicinity of glyA of genomic DNA of *Escherichia coli* cell line W3110. The obtained DNA fragments were digested with BamHI and PstI and with PstI and HindIII, respectively, which are restriction enzymes. Thus, approximately 850 bp and 750 bp fragments of each DNA fragment were obtained. The resulting DNA fragments were mixed with fragments obtained by digesting a temperature-sensitive cloning vector pTH18 cs1 (GenBank accession number: AB019610) (Hashimoto-Gotoh, T., Gene, 241, 185-191 (2000)) with BamHI and HindIII, followed by ligation using a ligase. The resultant was transformed into a DH5α cell line at 30° C. Thus, a transformant that was able to grow on an LB agar plate containing 10 μg/ml of chloramphenicol was obtained. The obtained colony was cultured overnight at 30° C. in an LB liquid medium containing 10 μg/ml of chloramphenicol so that a plasmid was recovered from the obtained cell bodies. The recovered plasmid was digested with PstI so as to be subjected to blunt-end treatment with T4DNA polymerase. Thereafter, the plasmid was ligated with a tetracycline-resistant gene derived from transposon Tn10.

The thus obtained plasmid was transformed into *Escherichia coli* W3110dsdA-deficient cell line at 30° C., followed by overnight culture at 30° C. on an LB agar plate containing 10 μg/ml of chloramphenicol and 50 μg/ml of tetracycline. Thus, a transformant was obtained. An LB liquid medium containing 50 μg/ml of tetracycline was inoculated with the obtained transformant, followed by overnight culture at 30° C. Next, the resultant was applied to an LB agar plate containing 50 μg/ml of tetracycline so as to obtain the culture cell bodies. Thus, colonies that grow at 42° C. were obtained. The obtained colonies were cultured overnight in an LB liquid medium containing 50 μg/ml of tetracycline at 30° C. The resultant was further applied to an LB agar plate containing 50 μg/ml of tetracycline so as to obtain colonies that grow at 42° C.

100 colonies were randomly picked up from the colonies that appeared. Each of them was allowed to grow on an LB agar plate containing 50 μg/ml of tetracycline and on an LB agar plate containing 10 μg/ml of chloramphenicol. Then, chloramphenicol-sensitive clones that exclusively grow on an LB agar plate containing tetracycline were selected. Further, fragments (of approximately 3.6 kbp) in the region in the vicinity of glyA were amplified by PCR from chromosome DNAs of these clones of interest. Then, a cell line in which glyA had been substituted with a tetracycline-resistant gene was selected. The obtained cell line was designated as a W3110dsdA/glyA-deficient cell line.

[13-2] (Effects of *Escherichia coli* in which the glyA Gene is Destroyed)

This *Escherichia coli* was transformed with plasmid pXDTA1, followed by culture in the same manner as that used in Example 10. Note that 20 mg/L of glycine was added in the case of flask culture and 2 g/L of glycine was added in the case of culture in a fermenter. During culture, glycine used was added at several different times.

L-serine production activity was examined in the same manner as that used in Example 9. D-serine optical purity was 97%.

Example 14

(Effects of Metal Salts)

300 mM EDTA (3.5 g; pH 7.5) was added to 100 g of frozen cell bodies of MT-11028 obtained in Example 10, followed by agitation at 4° C. for 1 hour. The resulting suspension (10 g) was suspended in 10 g of 0.5 M potassium phosphate buffer (pH 7.0) containing 20 mM each of manganese chloride, zinc sulfate, cobalt chloride, nickel chloride, calcium chloride, and ferrous chloride, followed by agitation at 4° C. for 1 hour.

Next, formaldehyde was added to the above suspension so as to account for 0.5% of the resultant, followed by agitation at 35° C. for 1 hour. Cell bodies (weighing 0.22 g as dry cell bodies) were taken from the above processed cell solution. The solution (9 g) used for enzyme activity measurement described in Example 10 was added thereto, followed by agitation at 35° C. for 20 hours. Then, the ratio between L-serine produced and residual D-serine was measured.

In a case in which a metal salt was used, optical purity of D-serine was 96% or more. In addition, 50% or more of the activity of the enzyme synthesizing D-serine from formaldehyde and glycine was maintained compared with the activity before organic solvent treatment, even in a case in which a metal salt was used.

Example 15

(Method for Improving Optical Purity Using L-Serine-Deaminase-Expressing *Escherichia coli*)

An LB medium (50 ml) was inoculated with *Escherichia coli* cell line K-12. After overnight culture at 30° C., harvest was carried out, followed by bacteriolysis using a lytic solution containing lysozyme (1 mg/ml). The resulting lysate was subjected to phenol treatment. Then, DNA was allowed to precipitate by ethanol precipitation in accordance with a usual method. The resulting DNA precipitate was recovered by spooling it onto a glass rod and washed so as to be used for PCR.

Primers used for PCR were oligonucleotides (obtained by custom synthesis from Hokkaido System Science Co., Ltd.) having nucleotide sequences set forth in SEQ ID NOS: 19 and 20, respectively, which were designed based on the known L-serine deaminase gene of *Escherichia coli* (GenBanak accession number: M28695). These primers had EcoRI and HindIII restriction enzyme recognition sequences near the 5' and 3' ends, respectively.

With the use of 0.025 ml of a PCR reaction solution containing 6 ng/μl each of chromosome DNAs of the aforementioned microorganisms and 3 μM each of the primers, PCR was carried out under the following conditions: denaturation at 96° C. for 1 minute, annealing at 55° C. for 30 seconds, and elongation reaction at 68° C. for 1 minute and 30 seconds for 35 reaction cycles.

The PCR reaction product and plasmid pUC18 (Takara Shuzo) were digested with EcoRI and HindIII, followed by ligation using Ligation High (TOYOBO). Thereafter, the obtained recombinant plasmid was used for transformation of *Escherichia coli* DH5α. The transformed cell line was cultured in an LB agar medium containing 50 μg/ml of ampicillin (Am) and X-Gal (5-bromo-4-chloro-3-indolyl-β-D-galactoside). Thus, an Am-resistant transformed cell line that was formed into a white colony was obtained. A plasmid was extracted from the thus obtained transformed cell line. In accordance with a usual method for base sequencing, the nucleotide sequence of the DNA fragment that had been introduced into the plasmid was confirmed to be identical to the sequence of a known *Escherichia coli* L-serine deaminase. The obtained expression plasmid was designated as pSDA1.

The *Escherichia coli* W3110dsdA/glyA-deficient cell line was transformed by a usual method using pSDA1. The obtained transformant was cultured in a fermenter in the same manner as that used in Example 13.

In the same manner as that used for the as comparative example in Example 12, reaction was carried out by adding 10 g of the aforementioned cell bodies to a reaction solution. The reaction solution was analyzed by HPLC. Thus, optical purity of D-serine in the reaction solution was found to be 99.9%.

All publications, patents, and patent applications cited herein are incorporated herein by reference in their entirety.

INDUSTRIAL APPLICABILITY

The present invention is useful as a method for producing D-serine from glycine and formaldehyde. In addition, D-serine obtained by the production method of the present invention is useful, for example, as a medicine intermediate of a starting material of D-cycloserine that is useful as an anti-tuberculous agent.

The invention claimed is:

1. An isolated protein comprising:

the amino acid sequence set forth in SEQ ID NO: 6 except that from one to five amino acid residues of the amino acid sequence of SEQ ID NO: 6 are substituted as follows:

a substitution at position 6 to Met or Ile,
a substitution at position 10 to Val or Ala,
a substitution at position 14 to Pro or Ala,
a substitution at position 17 to Pro or Ala,
a substitution at position 22 to Ala or Ser,
a substitution at position 23 to Arg or Ser,
a substitution at position 24 to Val or Ile,
a substitution at position 34 to Pro, Ala or Thr,
a substitution at position 35 to Pro or Ala,
a substitution at position 51 to Glu or Asp,
a substitution at position 68 to Leu or Arg,
a substitution at position 87 to Leu or Val,
a substitution at position 95 to Arg or Thr,
a substitution at position 107 to Ala or Gln,
a substitution at position 110 to Ala or Arg,
a substitution at position 113 to Ala or Gly,
a substitution at position 118 to Ala or Thr,
a substitution at position 121st to Ile, Met or Leu,
a substitution at position 129 to Ala, Gln or Glu,
a substitution at position 133 to Gln or Arg,
a substitution at position 134 to Ile or Leu,
a substitution at position 136 to His, Ala or Gln,
a substitution at position 139 to Ala or Thr,
a substitution at position 140 to Ala, Gln or Arg,
a substitution at position 165 to Thr or Leu,
a substitution at position 175 to Asp or Ala,
a substitution at position 179 to Leu or Val,
a substitution at position 180 to Asn or Thr,
a substitution at position 182 to Val or Ala,
a substitution at position 194 to Tyr or Leu,
a substitution at position 198 to Glu or Asp,
a substitution at position 202 to Ala or Gln,
a substitution at position 205 to Arg or Lys,
a substitution at position 214 to Tyr or His,
a substitution at position 215 to Ala or Gln,
a substitution at position 216 to Gln or Leu,
a substitution at position 221 to Ser or Asn,
a substitution at position 227 to Ile or Thr,
a substitution at position 236 to Val or Ala,
a substitution at position 266 to Asp or Asn,
a substitution at position 268 to Pro or Ala,
a substitution at position 270 to Thr, Lys or Ala,
a substitution at position 284 to Thr or Val,
a substitution at position 287 to Pro or Ala,
a substitution at position 288 to Asp or Gly,
a substitution at position 308 to Val or Ile,
a substitution at position 309 to Phe Tyr, or His,
a substitution at position 310 to Asp or Gly,
a substitution at position 311 to Ala or Glu,
a substitution at position 312 to Glu, Pro or Gln,
a substitution at position 315 to Thr or Gln,
a substitution at position 329 to Ala or Glu,
a substitution at position 331 to Asp or Gly,
a substitution at position 333 to Gln or Thr,
a substitution at position 334 to Pro or Ala,
a substitution at position 339 to Asp or Ala,
a substitution at position 340 to Thr or Val,
a substitution at position 342 to Arg or Leu,
a substitution at position 361 to Val or Tyr,
a substitution at position 362 to Arg or Lys,
a substitution at position 365 to Val or Ile,
a substitution at position 369 to Val or Ile, and
a substitution at position 373 to Ala or Ser, wherein said isolated protein has an enzyme activity of synthesizing D-serine from glycine and formaldehyde.

2. A method for producing D-serine, comprising allowing glycine to react with formaldehyde in the presence of a protein comprising the amino acid sequence set forth in SEQ ID NO:6; or the protein according to claim 1.

3. A transformant obtained by transforming a host cell using a recombinant DNA constructed by integrating DNA encoding a protein comprising the amino acid sequence set forth in SEQ ID NO:6; or the protein according to claim 1.

4. The transformant according to claim 3, wherein the host cell to be transformed is a microorganism.

5. The transformant according to claim 4, wherein the microorganism to be transformed is a D-serine-deaminase-deficient microorganism.

6. A method for producing D-serine, comprising allowing glycine to react with formaldehyde in the presence of the transformant according to claim 3, or a treated product thereof.

* * * * *

SEQUENCE LISTING

```
<160> NUMBER OF SEQ ID NOS: 20

<210> SEQ ID NO 1
<211> LENGTH: 43
<212> TYPE: DNA
<213> ORGANISM: Artificial Sequence
<220> FEATURE:
<223> OTHER INFORMATION: Oligonucleotide to act as a PCR primer for
      cloning of a novel DSA.
<220> FEATURE:
<221> NAME/KEY: misc_feature
<222> LOCATION: (43)..(43)
<223> OTHER INFORMATION: n is a, c, g, or t

<400> SEQUENCE: 1

gtggtaccac aaaaaggata aaacaatgtc ccaggaagtc atn                     43


<210> SEQ ID NO 2
<211> LENGTH: 31
<212> TYPE: DNA
<213> ORGANISM: Artificial Sequence
<220> FEATURE:
<223> OTHER INFORMATION: Oligonucleotide to act as a PCR primer for
      cloning of a novel DSA.

<400> SEQUENCE: 2

tcgaagcttt tagcgcgaga agccgcgcgc c                                  31


<210> SEQ ID NO 3
<211> LENGTH: 1140
```

```
<212> TYPE: DNA
<213> ORGANISM: Artificial Sequence
<220> FEATURE:
<223> OTHER INFORMATION: Sequence obtained from Achromobacter
      xylosoxidans ATCC9220 by PCR using primers SEQ ID NOs: 1 and 2

<400> SEQUENCE: 3

atg tcc cag gaa gtc atg cgc ggc att gtg ctg ccc ccg ccc gcc cag       48
Met Ser Gln Glu Val Met Arg Gly Ile Val Leu Pro Pro Pro Ala Gln
1               5                   10                  15

gcc ggc gat ccc ctg gcc agc gtc gac acg ccc agc ctg gtg ctg gac       96
Ala Gly Asp Pro Leu Ala Ser Val Asp Thr Pro Ser Leu Val Leu Asp
            20                  25                  30

ctg gcc gcg ttc gag gcc aac ctg cgc gcc atg cag gcc tgg gcc gac      144
Leu Ala Ala Phe Glu Ala Asn Leu Arg Ala Met Gln Ala Trp Ala Asp
        35                  40                  45

cgc cac gag gtc gcg ctg cgg ccg cac gcc aag gcc cac aag tgc ccc      192
Arg His Glu Val Ala Leu Arg Pro His Ala Lys Ala His Lys Cys Pro
    50                  55                  60

gag atc gcg cgc cgc cag ctg gcg ctg ggc gcg cgc gga atc tgt tgc      240
Glu Ile Ala Arg Arg Gln Leu Ala Leu Gly Ala Arg Gly Ile Cys Cys
65                  70                  75                  80

cag aag gtc agc gag gcc gtg ccc ttc gtg gcc gcc ggc atc acc gac      288
Gln Lys Val Ser Glu Ala Val Pro Phe Val Ala Ala Gly Ile Thr Asp
                85                  90                  95

atc cac atc agc aac gaa gtg gtc ggc ccg gcc aag ctg cgc ctc ttg      336
Ile His Ile Ser Asn Glu Val Val Gly Pro Ala Lys Leu Arg Leu Leu
            100                 105                 110

gcc cag ctg gcg cgc gcc gcc aag ctc agc gtc tgt gtc gac aac gcc      384
Ala Gln Leu Ala Arg Ala Ala Lys Leu Ser Val Cys Val Asp Asn Ala
        115                 120                 125

gcc aac ctg gcg cgg atc tcg cag gcc atg gcc gcg gcc ggc gcc gag      432
Ala Asn Leu Ala Arg Ile Ser Gln Ala Met Ala Ala Ala Gly Ala Glu
    130                 135                 140

atc gac gtg ctg gtg gaa gtg gac gtg ggc cag ggc cgc tgc ggc gtg      480
Ile Asp Val Leu Val Glu Val Asp Val Gly Gln Gly Arg Cys Gly Val
145                 150                 155                 160

tcc gac gac gcc acc gtg ctg gcg ctg gcg cag cag gcg cgc gac ctg      528
Ser Asp Asp Ala Thr Val Leu Ala Leu Ala Gln Gln Ala Arg Asp Leu
                165                 170                 175

ccg ggc gtg acc ttc gtc ggc ctg cag gcc tat cac ggc tcg gtg cag      576
Pro Gly Val Thr Phe Val Gly Leu Gln Ala Tyr His Gly Ser Val Gln
            180                 185                 190

cac ttg cgc acc cgg gac gaa cgc gcc gcc gtc tgc cgc cag gcc gcg      624
His Leu Arg Thr Arg Asp Glu Arg Ala Ala Val Cys Arg Gln Ala Ala
        195                 200                 205

cgc atc gcc gcg tcg tat caa ctg ctg ctg cgc gag agc ggc atc gcc      672
Arg Ile Ala Ala Ser Tyr Gln Leu Leu Leu Arg Glu Ser Gly Ile Ala
    210                 215                 220

tgc gac atc atc acc ggc ggc ggc acc ggc agc gcc gaa ttc gac gcc      720
Cys Asp Ile Ile Thr Gly Gly Gly Thr Gly Ser Ala Glu Phe Asp Ala
225                 230                 235                 240

gcc agc ggc gtc tac acc gaa ctg cag gcc ggt tcc tac gcc ttc atg      768
Ala Ser Gly Val Tyr Thr Glu Leu Gln Ala Gly Ser Tyr Ala Phe Met
                245                 250                 255

gac ggc gac tac ggc gcc aac gaa tgg gac ggc gcg ctc gcc ttc cag      816
Asp Gly Asp Tyr Gly Ala Asn Glu Trp Asp Gly Ala Leu Ala Phe Gln
            260                 265                 270

aac agc ctg ttc gtg ctg tcc acc gtg atg agc acc ccg gcg ccc gat      864
Asn Ser Leu Phe Val Leu Ser Thr Val Met Ser Thr Pro Ala Pro Asp
        275                 280                 285
```

```
cgc gtc atc ctc gac gcc ggc ctg aag tcc acc acc gcc gaa tgc ggc      912
Arg Val Ile Leu Asp Ala Gly Leu Lys Ser Thr Thr Ala Glu Cys Gly
    290                 295                 300

ccg ccc gcg atc cac ggc gcc cag ggc ctg caa tac gcc gcc atc aac      960
Pro Pro Ala Ile His Gly Ala Gln Gly Leu Gln Tyr Ala Ala Ile Asn
305                 310                 315                 320

gac gaa cac ggc gtg gtg cgc gtg gcg ccc gac gcg cag ccg ccg gcg     1008
Asp Glu His Gly Val Val Arg Val Ala Pro Asp Ala Gln Pro Pro Ala
                325                 330                 335

ctg ggc gac acg ctg ctg ctg gtg ccc tcg cac gtc gac ccc acc ttc     1056
Leu Gly Asp Thr Leu Leu Leu Val Pro Ser His Val Asp Pro Thr Phe
            340                 345                 350

aac ctg cac gat ggg ctg gtg gtg tat cgc gac ggc atc gtg cag gac     1104
Asn Leu His Asp Gly Leu Val Val Tyr Arg Asp Gly Ile Val Gln Asp
        355                 360                 365

atc tgg gag atc tcg gcg cgc ggc ttc tcg cgc taa                     1140
Ile Trp Glu Ile Ser Ala Arg Gly Phe Ser Arg
    370                 375


<210> SEQ ID NO 4
<211> LENGTH: 379
<212> TYPE: PRT
<213> ORGANISM: Artificial Sequence
<220> FEATURE:
<223> OTHER INFORMATION: Protein encoded by sequence obtained from
      Achromobacter xylosoxidans ATCC9220 by PCR with SEQ ID NOs: 1 and
      2

<400> SEQUENCE: 4

Met Ser Gln Glu Val Met Arg Gly Ile Val Leu Pro Pro Pro Ala Gln
1               5                   10                  15

Ala Gly Asp Pro Leu Ala Ser Val Asp Thr Pro Ser Leu Val Leu Asp
            20                  25                  30

Leu Ala Ala Phe Glu Ala Asn Leu Arg Ala Met Gln Ala Trp Ala Asp
        35                  40                  45

Arg His Glu Val Ala Leu Arg Pro His Ala Lys Ala His Lys Cys Pro
    50                  55                  60

Glu Ile Ala Arg Arg Gln Leu Ala Leu Gly Ala Arg Gly Ile Cys Cys
65                  70                  75                  80

Gln Lys Val Ser Glu Ala Val Pro Phe Val Ala Ala Gly Ile Thr Asp
                85                  90                  95

Ile His Ile Ser Asn Glu Val Val Gly Pro Ala Lys Leu Arg Leu Leu
            100                 105                 110

Ala Gln Leu Ala Arg Ala Ala Lys Leu Ser Val Cys Val Asp Asn Ala
        115                 120                 125

Ala Asn Leu Ala Arg Ile Ser Gln Ala Met Ala Ala Ala Gly Ala Glu
    130                 135                 140

Ile Asp Val Leu Val Glu Val Asp Val Gly Gln Gly Arg Cys Gly Val
145                 150                 155                 160

Ser Asp Asp Ala Thr Val Leu Ala Leu Ala Gln Gln Ala Arg Asp Leu
                165                 170                 175

Pro Gly Val Thr Phe Val Gly Leu Gln Ala Tyr His Gly Ser Val Gln
            180                 185                 190

His Leu Arg Thr Arg Asp Glu Arg Ala Ala Val Cys Arg Gln Ala Ala
        195                 200                 205

Arg Ile Ala Ala Ser Tyr Gln Leu Leu Leu Arg Glu Ser Gly Ile Ala
    210                 215                 220
```

-continued

```
Cys Asp Ile Ile Thr Gly Gly Gly Thr Gly Ser Ala Glu Phe Asp Ala
225                 230                 235                 240

Ala Ser Gly Val Tyr Thr Glu Leu Gln Ala Gly Ser Tyr Ala Phe Met
                245                 250                 255

Asp Gly Asp Tyr Gly Ala Asn Glu Trp Asp Gly Ala Leu Ala Phe Gln
            260                 265                 270

Asn Ser Leu Phe Val Leu Ser Thr Val Met Ser Thr Pro Ala Pro Asp
        275                 280                 285

Arg Val Ile Leu Asp Ala Gly Leu Lys Ser Thr Thr Ala Glu Cys Gly
    290                 295                 300

Pro Pro Ala Ile His Gly Ala Gln Gly Leu Gln Tyr Ala Ala Ile Asn
305                 310                 315                 320

Asp Glu His Gly Val Val Arg Val Ala Pro Asp Ala Gln Pro Pro Ala
                325                 330                 335

Leu Gly Asp Thr Leu Leu Leu Val Pro Ser His Val Asp Pro Thr Phe
            340                 345                 350

Asn Leu His Asp Gly Leu Val Val Tyr Arg Asp Gly Ile Val Gln Asp
        355                 360                 365

Ile Trp Glu Ile Ser Ala Arg Gly Phe Ser Arg
    370                 375


<210> SEQ ID NO 5
<211> LENGTH: 1140
<212> TYPE: DNA
<213> ORGANISM: Artificial Sequence
<220> FEATURE:
<223> OTHER INFORMATION: Sequence obtained from Achromobacter
      xylosoxidans NBRC13495 by PCR using primers SEQ ID NO: 1 and 2

<400> SEQUENCE: 5

atg tcc cag gaa gtc ata cgc ggc ata gcg ctg ccc ccg ccc gcg caa       48
Met Ser Gln Glu Val Ile Arg Gly Ile Ala Leu Pro Pro Pro Ala Gln
1               5                   10                  15

ccg ggc gac ccg ttg gcc cgc gtc gac acg ccc agc ctg gtg ctg gac       96
Pro Gly Asp Pro Leu Ala Arg Val Asp Thr Pro Ser Leu Val Leu Asp
            20                  25                  30

ctg acg ccc ttt gag gcc aat ctg cgc gcc atg caa gcc tgg gcc gac      144
Leu Thr Pro Phe Glu Ala Asn Leu Arg Ala Met Gln Ala Trp Ala Asp
        35                  40                  45

cgt cac gac gtt gcc ttg cgt ccg cat gcc aag gcg cac aaa tgc ccc      192
Arg His Asp Val Ala Leu Arg Pro His Ala Lys Ala His Lys Cys Pro
    50                  55                  60

gag atc gcg ttg cgg cag ctt gcg ctg ggc gcg cgt ggc att tgc tgc      240
Glu Ile Ala Leu Arg Gln Leu Ala Leu Gly Ala Arg Gly Ile Cys Cys
65                  70                  75                  80

cag aag gtc agc gaa gcc ctg ccc ttt gtg gcg gcc ggc att cgc gac      288
Gln Lys Val Ser Glu Ala Leu Pro Phe Val Ala Ala Gly Ile Arg Asp
                85                  90                  95

atc cac atc agc aat gaa gtc gtc ggg ccg caa aag ctg gcc ttg ctg      336
Ile His Ile Ser Asn Glu Val Val Gly Pro Gln Lys Leu Ala Leu Leu
            100                 105                 110

gcg caa ctg gcg cgc acg gcc aag atg agc gtc tgt gtc gat aac gcg      384
Ala Gln Leu Ala Arg Thr Ala Lys Met Ser Val Cys Val Asp Asn Ala
        115                 120                 125

cag aac ctg gcg cag att tcc cac gcc atg gcg cag gcc ggg gcc gag      432
Gln Asn Leu Ala Gln Ile Ser His Ala Met Ala Gln Ala Gly Ala Glu
    130                 135                 140

atc gat gtg ctg gtg gaa gtc gat gtc gga caa ggc cgt tgc ggc gtg      480
Ile Asp Val Leu Val Glu Val Asp Val Gly Gln Gly Arg Cys Gly Val
```

```
145                 150                 155                 160

tct gac gac gcc ttg gtg ctg gcg ctg gcg cag cag gcg cgg gac ttg      528
Ser Asp Asp Ala Leu Val Leu Ala Leu Ala Gln Gln Ala Arg Asp Leu
                165                 170                 175

ccc ggc gtg aac ttc gtg ggg ctg cag gcg tat cac ggc tcg gtt cag      576
Pro Gly Val Asn Phe Val Gly Leu Gln Ala Tyr His Gly Ser Val Gln
            180                 185                 190

cac tac cgc acg cgc gaa gaa cgc gca cag gtc tgc aag caa gcg gcg      624
His Tyr Arg Thr Arg Glu Glu Arg Ala Gln Val Cys Lys Gln Ala Ala
        195                 200                 205

cgc atc gcg gcg tcc cat gcg cag ctc ttg cgc gag aac ggc att gcg      672
Arg Ile Ala Ala Ser His Ala Gln Leu Leu Arg Glu Asn Gly Ile Ala
    210                 215                 220

tgc gac atc atc aca gga ggc ggc acg ggc agc gcg gag ttc gac gcg      720
Cys Asp Ile Ile Thr Gly Gly Gly Thr Gly Ser Ala Glu Phe Asp Ala
225                 230                 235                 240

gca agc ggc gtc tac acc gaa ttg cag gcg ggt tca tac gcg ttc atg      768
Ala Ser Gly Val Tyr Thr Glu Leu Gln Ala Gly Ser Tyr Ala Phe Met
                245                 250                 255

gat ggc gac tac ggc gcc aac gaa tgg gac ggc ccg ctc acg ttc cag      816
Asp Gly Asp Tyr Gly Ala Asn Glu Trp Asp Gly Pro Leu Thr Phe Gln
            260                 265                 270

aac agc ctg ttc gtg ttg tcc acg gtg atg agc gtg ccc gcc gcc gac      864
Asn Ser Leu Phe Val Leu Ser Thr Val Met Ser Val Pro Ala Ala Asp
        275                 280                 285

cgc gtg atc ctg gat gcg ggc ttg aaa tcg act acc gcc gaa tgc ggc      912
Arg Val Ile Leu Asp Ala Gly Leu Lys Ser Thr Thr Ala Glu Cys Gly
    290                 295                 300

ccg cct gcc gtc ttt gat gct gaa ggg ctg acc tat gcc gcc atc aac      960
Pro Pro Ala Val Phe Asp Ala Glu Gly Leu Thr Tyr Ala Ala Ile Asn
305                 310                 315                 320

gac gag cac ggc gtg gtg cgc gtg gcg cct ggc gcc acc gca ccc gcg     1008
Asp Glu His Gly Val Val Arg Val Ala Pro Gly Ala Thr Ala Pro Ala
                325                 330                 335

ttg ggt gat gtg ctg cgc ctg gtg ccg tcg cac gtg gac ccc acc ttc     1056
Leu Gly Asp Val Leu Arg Leu Val Pro Ser His Val Asp Pro Thr Phe
            340                 345                 350

aac ttg cat gac ggg ctg gtc gtg gtg cgg gac ggc gtg gtg caa gac     1104
Asn Leu His Asp Gly Leu Val Val Val Arg Asp Gly Val Val Gln Asp
        355                 360                 365

atc tgg gag atc gcg gcg cgc ggc ttt tcg cgc taa                     1140
Ile Trp Glu Ile Ala Ala Arg Gly Phe Ser Arg
    370                 375


<210> SEQ ID NO 6
<211> LENGTH: 379
<212> TYPE: PRT
<213> ORGANISM: Artificial Sequence
<220> FEATURE:
<223> OTHER INFORMATION: Protein encoded by sequence obtained from
      Achromobacter xylosoxidans NBRC13495 by PCR with SEQ ID NOs: 1
      and 2

<400> SEQUENCE: 6

Met Ser Gln Glu Val Ile Arg Gly Ile Ala Leu Pro Pro Pro Ala Gln
1               5                   10                  15

Pro Gly Asp Pro Leu Ala Arg Val Asp Thr Pro Ser Leu Val Leu Asp
            20                  25                  30

Leu Thr Pro Phe Glu Ala Asn Leu Arg Ala Met Gln Ala Trp Ala Asp
        35                  40                  45
```

-continued

```
Arg His Asp Val Ala Leu Arg Pro His Ala Lys Ala His Lys Cys Pro
    50                  55                  60

Glu Ile Ala Leu Arg Gln Leu Ala Leu Gly Ala Arg Gly Ile Cys Cys
65                  70                  75                  80

Gln Lys Val Ser Glu Ala Leu Pro Phe Val Ala Ala Gly Ile Arg Asp
                85                  90                  95

Ile His Ile Ser Asn Glu Val Val Gly Pro Gln Lys Leu Ala Leu Leu
            100                 105                 110

Ala Gln Leu Ala Arg Thr Ala Lys Met Ser Val Cys Val Asp Asn Ala
        115                 120                 125

Gln Asn Leu Ala Gln Ile Ser His Ala Met Ala Gln Ala Gly Ala Glu
    130                 135                 140

Ile Asp Val Leu Val Glu Val Asp Val Gly Gln Gly Arg Cys Gly Val
145                 150                 155                 160

Ser Asp Asp Ala Leu Val Leu Ala Leu Ala Gln Gln Ala Arg Asp Leu
                165                 170                 175

Pro Gly Val Asn Phe Val Gly Leu Gln Ala Tyr His Gly Ser Val Gln
            180                 185                 190

His Tyr Arg Thr Arg Glu Glu Arg Ala Gln Val Cys Lys Gln Ala Ala
        195                 200                 205

Arg Ile Ala Ala Ser His Ala Gln Leu Leu Arg Glu Asn Gly Ile Ala
    210                 215                 220

Cys Asp Ile Ile Thr Gly Gly Gly Thr Gly Ser Ala Glu Phe Asp Ala
225                 230                 235                 240

Ala Ser Gly Val Tyr Thr Glu Leu Gln Ala Gly Ser Tyr Ala Phe Met
                245                 250                 255

Asp Gly Asp Tyr Gly Ala Asn Glu Trp Asp Gly Pro Leu Thr Phe Gln
            260                 265                 270

Asn Ser Leu Phe Val Leu Ser Thr Val Met Ser Val Pro Ala Ala Asp
        275                 280                 285

Arg Val Ile Leu Asp Ala Gly Leu Lys Ser Thr Thr Ala Glu Cys Gly
    290                 295                 300

Pro Pro Ala Val Phe Asp Ala Glu Gly Leu Thr Tyr Ala Ala Ile Asn
305                 310                 315                 320

Asp Glu His Gly Val Val Arg Val Ala Pro Gly Ala Thr Ala Pro Ala
                325                 330                 335

Leu Gly Asp Val Leu Arg Leu Val Pro Ser His Val Asp Pro Thr Phe
            340                 345                 350

Asn Leu His Asp Gly Leu Val Val Val Arg Asp Gly Val Val Gln Asp
        355                 360                 365

Ile Trp Glu Ile Ala Ala Arg Gly Phe Ser Arg
    370                 375


<210> SEQ ID NO 7
<211> LENGTH: 1140
<212> TYPE: DNA
<213> ORGANISM: Artificial Sequence
<220> FEATURE:
<223> OTHER INFORMATION: Sequence obtained from Achromobacter
      denitrificans NBRC15125 by PCR using primers SEQ ID NO: 1 and 2

<400> SEQUENCE: 7

atg tcc cag gaa gtc ata cgc ggc ata gcg ctg ccc ccg gcg gcc cag       48
Met Ser Gln Glu Val Ile Arg Gly Ile Ala Leu Pro Pro Ala Ala Gln
1               5                   10                  15

ccg ggc gat ccc ttg tcc cgg atc gac acg ccc agc ctg gtg ctg gac       96
```

-continued

```
Pro Gly Asp Pro Leu Ser Arg Ile Asp Thr Pro Ser Leu Val Leu Asp
            20                  25                  30

ctg ccg gcc ttc gag gcg aat ctg cgc gcc atg cag gcc tgg gcc gac      144
Leu Pro Ala Phe Glu Ala Asn Leu Arg Ala Met Gln Ala Trp Ala Asp
        35                  40                  45

cgg cac gag gtg gcc ctg cgg ccc cac gcc aag gcg cac aag tgc ccg      192
Arg His Glu Val Ala Leu Arg Pro His Ala Lys Ala His Lys Cys Pro
    50                  55                  60

gaa atc gcc ttg cgc cag ctg gcc ctg ggc gcg cgc ggc atc tgc tgc      240
Glu Ile Ala Leu Arg Gln Leu Ala Leu Gly Ala Arg Gly Ile Cys Cys
65                  70                  75                  80

cag aag gtc agc gaa gcc ctg ccc ttc gtg gcc gcc ggc atc cgc gac      288
Gln Lys Val Ser Glu Ala Leu Pro Phe Val Ala Ala Gly Ile Arg Asp
                85                  90                  95

atc cac atc agc aac gaa gtg gtc ggc ccg gcc aag ctg gcg ctg ctg      336
Ile His Ile Ser Asn Glu Val Val Gly Pro Ala Lys Leu Ala Leu Leu
            100                 105                 110

ggc caa ctg gcg cgc gcc gcc aag atc agc gtg tgc gtg gac aac gcc      384
Gly Gln Leu Ala Arg Ala Ala Lys Ile Ser Val Cys Val Asp Asn Ala
        115                 120                 125

gaa aac ctg gcg cag ctg tcg gcc gcc atg acc cgg gcc ggc gcc gag      432
Glu Asn Leu Ala Gln Leu Ser Ala Ala Met Thr Arg Ala Gly Ala Glu
    130                 135                 140

atc gac gtg ctg gtc gag gtg gac gtg ggc cag ggc cgc tgc ggc gtg      480
Ile Asp Val Leu Val Glu Val Asp Val Gly Gln Gly Arg Cys Gly Val
145                 150                 155                 160

tcc gac gac gcc acc gtg ctg gcg ctg gcg cag cag gcc cgc gcc ctg      528
Ser Asp Asp Ala Thr Val Leu Ala Leu Ala Gln Gln Ala Arg Ala Leu
                165                 170                 175

ccc ggc ctg aat ttc gcg ggg ctg cag gcc tac cac ggc tcg gtg cag      576
Pro Gly Leu Asn Phe Ala Gly Leu Gln Ala Tyr His Gly Ser Val Gln
            180                 185                 190

cac tac cgc acg cgc gaa gag cgc gcc gcc gtc tgc cgg cag gcc gcg      624
His Tyr Arg Thr Arg Glu Glu Arg Ala Ala Val Cys Arg Gln Ala Ala
        195                 200                 205

cgc atc gcc gcg tcc tat gcg cag ctg ctg cgc gag agc ggc atc gcc      672
Arg Ile Ala Ala Ser Tyr Ala Gln Leu Leu Arg Glu Ser Gly Ile Ala
    210                 215                 220

tgc gac acc atc acc ggc ggc ggc acg ggc agc gtg gaa ttc gac gcg      720
Cys Asp Thr Ile Thr Gly Gly Gly Thr Gly Ser Val Glu Phe Asp Ala
225                 230                 235                 240

gcc agc ggc gtc tac acc gag ctg cag gcc ggt tcc tac gcc ttc atg      768
Ala Ser Gly Val Tyr Thr Glu Leu Gln Ala Gly Ser Tyr Ala Phe Met
                245                 250                 255

gac ggc gac tac ggc gcc aac gaa tgg aac ggc ccg ctg aag ttc cag      816
Asp Gly Asp Tyr Gly Ala Asn Glu Trp Asn Gly Pro Leu Lys Phe Gln
            260                 265                 270

aac agc ctc ttc gtg ctg tcc acc gtc atg agc acg ccc gcc cct ggg      864
Asn Ser Leu Phe Val Leu Ser Thr Val Met Ser Thr Pro Ala Pro Gly
        275                 280                 285

cgt gtc atc ctg gac gcg ggc ctg aag tcc acc acg gcc gaa tgc ggc      912
Arg Val Ile Leu Asp Ala Gly Leu Lys Ser Thr Thr Ala Glu Cys Gly
    290                 295                 300

ccg ccc gcg gtc tac ggc gag ccg ggg ctc acc tac gcg gcc atc aac      960
Pro Pro Ala Val Tyr Gly Glu Pro Gly Leu Thr Tyr Ala Ala Ile Asn
305                 310                 315                 320

gat gaa cac ggc gtg gtg cgc gtg gaa ccc ggc gcg cag gcg ccc gcc     1008
Asp Glu His Gly Val Val Arg Val Glu Pro Gly Ala Gln Ala Pro Ala
                325                 330                 335
```

-continued

```
ctg ggc gcc gtg ctg cgc ctg gtg cct tcg cac gtc gac ccc acc ttc     1056
Leu Gly Ala Val Leu Arg Leu Val Pro Ser His Val Asp Pro Thr Phe
            340                 345                 350

aac ctg cac gac ggc ctg gtg gtg gtg aag gac ggc gtg gtg cag gac     1104
Asn Leu His Asp Gly Leu Val Val Val Lys Asp Gly Val Val Gln Asp
        355                 360                 365

gtc tgg gaa atc gcg gcg cgc ggc ttt tcg cgc taa                     1140
Val Trp Glu Ile Ala Ala Arg Gly Phe Ser Arg
    370                 375


<210> SEQ ID NO 8
<211> LENGTH: 379
<212> TYPE: PRT
<213> ORGANISM: Artificial Sequence
<220> FEATURE:
<223> OTHER INFORMATION: Protein encoded by sequence obtained from
      Achromobacter denitrificans NBRC15125 by PCR with SEQ ID NOs:
      1 and 2

<400> SEQUENCE: 8

Met Ser Gln Glu Val Ile Arg Gly Ile Ala Leu Pro Pro Ala Ala Gln
1               5                   10                  15

Pro Gly Asp Pro Leu Ser Arg Ile Asp Thr Pro Ser Leu Val Leu Asp
            20                  25                  30

Leu Pro Ala Phe Glu Ala Asn Leu Arg Ala Met Gln Ala Trp Ala Asp
        35                  40                  45

Arg His Glu Val Ala Leu Arg Pro His Ala Lys Ala His Lys Cys Pro
    50                  55                  60

Glu Ile Ala Leu Arg Gln Leu Ala Leu Gly Ala Arg Gly Ile Cys Cys
65                  70                  75                  80

Gln Lys Val Ser Glu Ala Leu Pro Phe Val Ala Ala Gly Ile Arg Asp
                85                  90                  95

Ile His Ile Ser Asn Glu Val Val Gly Pro Ala Lys Leu Ala Leu Leu
            100                 105                 110

Gly Gln Leu Ala Arg Ala Ala Lys Ile Ser Val Cys Val Asp Asn Ala
        115                 120                 125

Glu Asn Leu Ala Gln Leu Ser Ala Ala Met Thr Arg Ala Gly Ala Glu
    130                 135                 140

Ile Asp Val Leu Val Glu Val Asp Val Gly Gln Gly Arg Cys Gly Val
145                 150                 155                 160

Ser Asp Asp Ala Thr Val Leu Ala Leu Ala Gln Gln Ala Arg Ala Leu
                165                 170                 175

Pro Gly Leu Asn Phe Ala Gly Leu Gln Ala Tyr His Gly Ser Val Gln
            180                 185                 190

His Tyr Arg Thr Arg Glu Glu Arg Ala Ala Val Cys Arg Gln Ala Ala
        195                 200                 205

Arg Ile Ala Ala Ser Tyr Ala Gln Leu Leu Arg Glu Ser Gly Ile Ala
    210                 215                 220

Cys Asp Thr Ile Thr Gly Gly Gly Thr Gly Ser Val Glu Phe Asp Ala
225                 230                 235                 240

Ala Ser Gly Val Tyr Thr Glu Leu Gln Ala Gly Ser Tyr Ala Phe Met
                245                 250                 255

Asp Gly Asp Tyr Gly Ala Asn Glu Trp Asn Gly Pro Leu Lys Phe Gln
            260                 265                 270

Asn Ser Leu Phe Val Leu Ser Thr Val Met Ser Thr Pro Ala Pro Gly
        275                 280                 285

Arg Val Ile Leu Asp Ala Gly Leu Lys Ser Thr Thr Ala Glu Cys Gly
```

-continued

```
    290                 295                 300

Pro Pro Ala Val Tyr Gly Glu Pro Gly Leu Thr Tyr Ala Ala Ile Asn
305                 310                 315                 320

Asp Glu His Gly Val Val Arg Val Glu Pro Gly Ala Gln Ala Pro Ala
                325                 330                 335

Leu Gly Ala Val Leu Arg Leu Val Pro Ser His Val Asp Pro Thr Phe
            340                 345                 350

Asn Leu His Asp Gly Leu Val Val Val Lys Asp Gly Val Val Gln Asp
        355                 360                 365

Val Trp Glu Ile Ala Ala Arg Gly Phe Ser Arg
    370                 375
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 9
aactgcagtt gccattccgc tatgtacc 28

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 10
ggtctagaaa tgacagcagg aatgtgc 27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 11
agtctagaac gcagcatcgc aatcc 25

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 12
atggtacctt actctggagc gatcgtcc 28

<210> SEQ ID NO 13
<211> LENGTH: 48
<212> TYPE: DNA
<213> ORGANISM: Artificial Sequence
<220> FEATURE:
<223> OTHER INFORMATION: Oligonucleotide to act as a PCR primer for cloning of DAT of Xanthomonas oryzae IAM1657.

<400> SEQUENCE: 13
ggggtaccac aaaaaggata aaacaatgtc ccaggaagtc atacgcgg 48

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide to act as a PCR primer for cloning of DTA of Xanthomonas oryzae IAM1657.

<400> SEQUENCE: 14
tcgaagcttt tagcgcgaaa agccgcgcgc cgcga 35

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 15
taggatcctc tgctggaaga gaagctcgg 29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 16
atctgcagca atgtgctcgt tgttcatgcc 30

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 17
atctgcagtt ggcctttata ggcggtcctg t 31

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 18
atgtaagctt tcgcgagtac cttcccaacc ac 32

<210> SEQ ID NO 19
<211> LENGTH: 50
<212> TYPE: DNA
<213> ORGANISM: Artificial Sequence
<220> FEATURE:
<223> OTHER INFORMATION: Oligonucleotide to act as a PCR primer for cloning of sdaA of Escherichia coli K12.

<400> SEQUENCE: 19
gtgaattcac aaaaaggata aaacaatgat tagtctattc gacatgttta 50

<210> SEQ ID NO 20
<211> LENGTH: 33
<212> TYPE: DNA
<213> ORGANISM: Artificial Sequence
<220> FEATURE:

-continued

```
<223> OTHER INFORMATION: Oligonucleotide to act as a PCR primer for
      cloning of sdaA of Escherichia coli K12.

<400> SEQUENCE: 20

tcgaagcttt tagtcacact ggactttgat tgc                            33
```